United States Patent [19]

Suzuki et al.

[11] Patent Number: 5,656,928
[45] Date of Patent: Aug. 12, 1997

[54] SURROUNDING STATE MEASURING APPARATUS UTILIZING AN IMPEDANCE ELEMENT

[75] Inventors: Koji Suzuki, Yokohama; Junichi Intoh, Tokyo, both of Japan

[73] Assignee: Canon Kabushiki Kaisha, Tokyo, Japan

[21] Appl. No.: 460,835

[22] Filed: Jun. 5, 1995

Related U.S. Application Data

[63] Continuation of Ser. No. 984,096, Dec. 1, 1992, abandoned.

[30] Foreign Application Priority Data

Dec. 2, 1991 [JP] Japan ................................. 3-317777
Feb. 28, 1992 [JP] Japan ................................. 4-043355

[51] Int. Cl.⁶ .................................................. G01N 27/02
[52] U.S. Cl. ...................... 324/71.1; 324/693; 324/705; 324/712; 73/335.02; 73/335.05; 364/557
[58] Field of Search .................................. 324/71.1, 606, 324/607, 691, 693, 705, 712, 720; 73/335.02, 335.05; 364/557, 558

[56] References Cited

U.S. PATENT DOCUMENTS

| | | | |
|---|---|---|---|
| 2,873,607 | 2/1959 | Van Kuyk | 73/335.02 |
| 3,713,337 | 1/1973 | Stroman | 73/861.42 |
| 4,161,880 | 7/1979 | Prosky | 364/557 |
| 4,216,675 | 8/1980 | Nagata et al. | 324/720 |
| 4,362,988 | 12/1982 | Weimer | 324/607 |
| 4,369,661 | 1/1983 | Gibb | 324/720 |
| 4,816,748 | 3/1989 | Tazawa et al. | 324/667 |
| 4,844,788 | 7/1989 | Takahashi et al. | 204/406 |
| 5,027,077 | 6/1991 | Yanagisawa et al. | 324/606 |
| 5,105,294 | 4/1992 | Degura et al. | 359/154 |
| 5,113,278 | 5/1992 | Degura et al. | 359/154 |
| 5,519,325 | 5/1996 | Park | 324/607 |

FOREIGN PATENT DOCUMENTS

| | | | |
|---|---|---|---|
| 108325 | 5/1984 | European Pat. Off. | G01K 1/02 |
| 2222261 | 2/1990 | United Kingdom | C01N 27/12 |

OTHER PUBLICATIONS

Patent Abstracts of Japan, Publ. No. JP62062230, vol. 011256, "A/D Converter for Photometer Adapted Measure Light About Multiple Pieces of Information", Shuji et al. (Aug. 20, 1987).

*Primary Examiner*—Kenneth A. Wieder
*Assistant Examiner*—Glenn W. Brown
*Attorney, Agent, or Firm*—Fitzpatrick, Cella, Harper & Scinto

[57] ABSTRACT

Measuring apparatus includes a first element having its impedance dependant on the state of its surroundings and a second element having a variable impedance connected to the first element. A voltage at the connection point between the first and second elements is converted into a digital value and the impedance of the second element is set based on the converted digital value. The surrounding state (e.g., humidity) is determined based on the converted digital value.

18 Claims, 40 Drawing Sheets

1

SURROUNDING STATE MEASURING APPARATUS UTILIZING AN IMPEDANCE ELEMENT

This application is a continuation of application Ser. No. 07/984,096 filed Dec. 1, 1992, now abandoned.

BACKGROUND OF THE INVENTION

1. Field of the Invention

The present invention relates to a measuring apparatus for performing the measurement using an element having its impedance varied depending on the surrounding state.

2. Related Background Art

Conventionally, it has been quite difficult to measure the humidity in a wide range from high to low temperatures at a high precision. This is because the output of a humidity sensor has a high-order γ characteristic as shown in FIG. 2, which makes difficult the linear approximation in a wide range.

It is the common practice to make use of the voltage-current characteristics of a diode for the linear conversion, but to compensate for the difference between the actual sensor characteristic and the diode characteristic, it was necessary to individually adjust a respective combination. The precision, however, is insufficient to make the linear conversion for a wide range of humidity.

In addition, a method has been proposed in which a high-order approximate curve is obtained by the least square method, using a CPU, and a sensor output is substituted thereinto to make the linear approximation, and has been already put to practical use, but in order to make the measurement at a high precision in a wide range, the higher resolution in a measurement circuit is required, thereby requiring higher bits of CPU or A/D converter, or an increase in the processing time of CPU.

However, as shown in FIG. 2, the output of a sensor may vary from 1 KΩ to 10 MΩ or greater with respect to the relative humidity of 20 to 95%. If a measurement is tried at a low humidity of 10% or less, a high resistance of 100 MΩ or greater is anticipated. To have a measurement precision for the relative humidity of 5% or less, a precision (resolution) of 0.3 KΩ is necessary at 60° C. and near 95%, so that a resolution of not more than 1/330000 is required in a detection circuit, A/D converter and CPU, whereby it was impossible to actually measure the humidity in such a wide range at a high precision.

Also, an apparatus has been proposed in which a humidity sensor having its resistance varied with the humidity and a condenser are connected in series to apply a DC voltage between the humidity sensor and the condenser, whereby the time until the condenser voltage reaches a predetermined value and the sensor characteristic are calculated by using a linear approximate expression.

However, in particular, if the range in the low humidity side is expanded, a problem arises that the resistance of humidity sensor and thus the charging time will increase. For example, at 25° C. and near 10%, the resistance of humidity sensor is 10 GΩ or greater, whereby even if the capacity of condenser to be charged is decreased to about 30 PF, a charging time as long as about 300 ms is necessary. If the charging time is expanded to such a level, the humidity sensor is effectively equivalent to a state in which a DC voltage is applied, so that the humidity sensor may degrade rapidly due to the deflection of internal ions.

SUMMARY OF THE INVENTION

It is an object of the present invention to provide a measuring apparatus which can resolve the aforementioned drawbacks.

It is another object of the present invention to provide an improved measuring apparatus.

It is further object of the present invention to provide a measuring apparatus at a high precision in a wide range.

It is still further object of the present invention to provide a simple and inexpensive measuring apparatus without needs of any troublesome process such as the adjustment.

Also, it is another object of the present invention to provide a measuring apparatus in which a detecting element for use in the measuring is prevented from degrading.

Other objects and features of the present invention will be apparent from the following description and the attached drawings.

DETAILED DESCRIPTION OF THE PREFERRED EMBODIMENTS

EMBODIMENT 1

Figure 1:
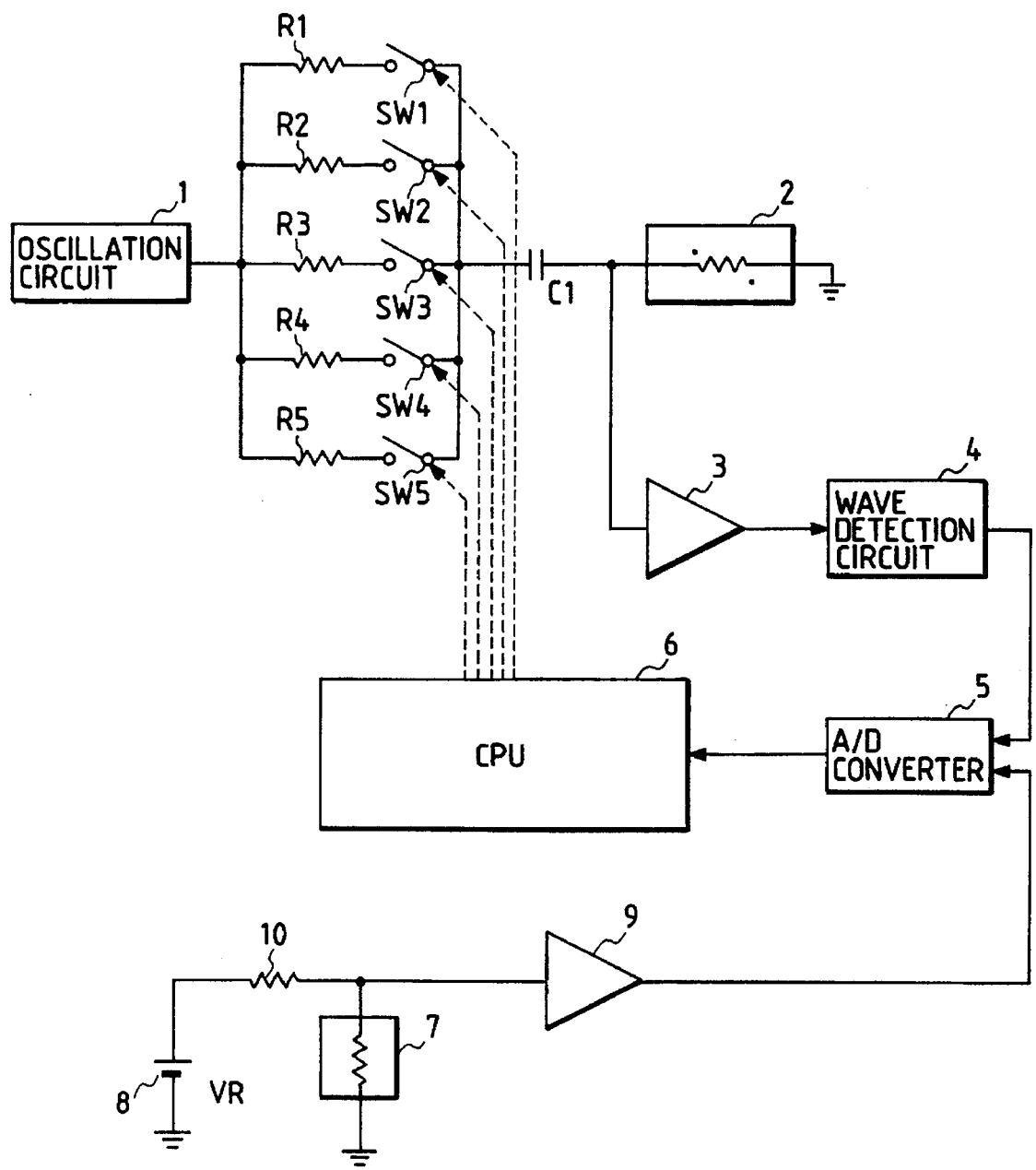
FIG. 1 is a circuit configuration diagram of a humidity measuring apparatus according to an embodiment of the present invention.
Figure 4:
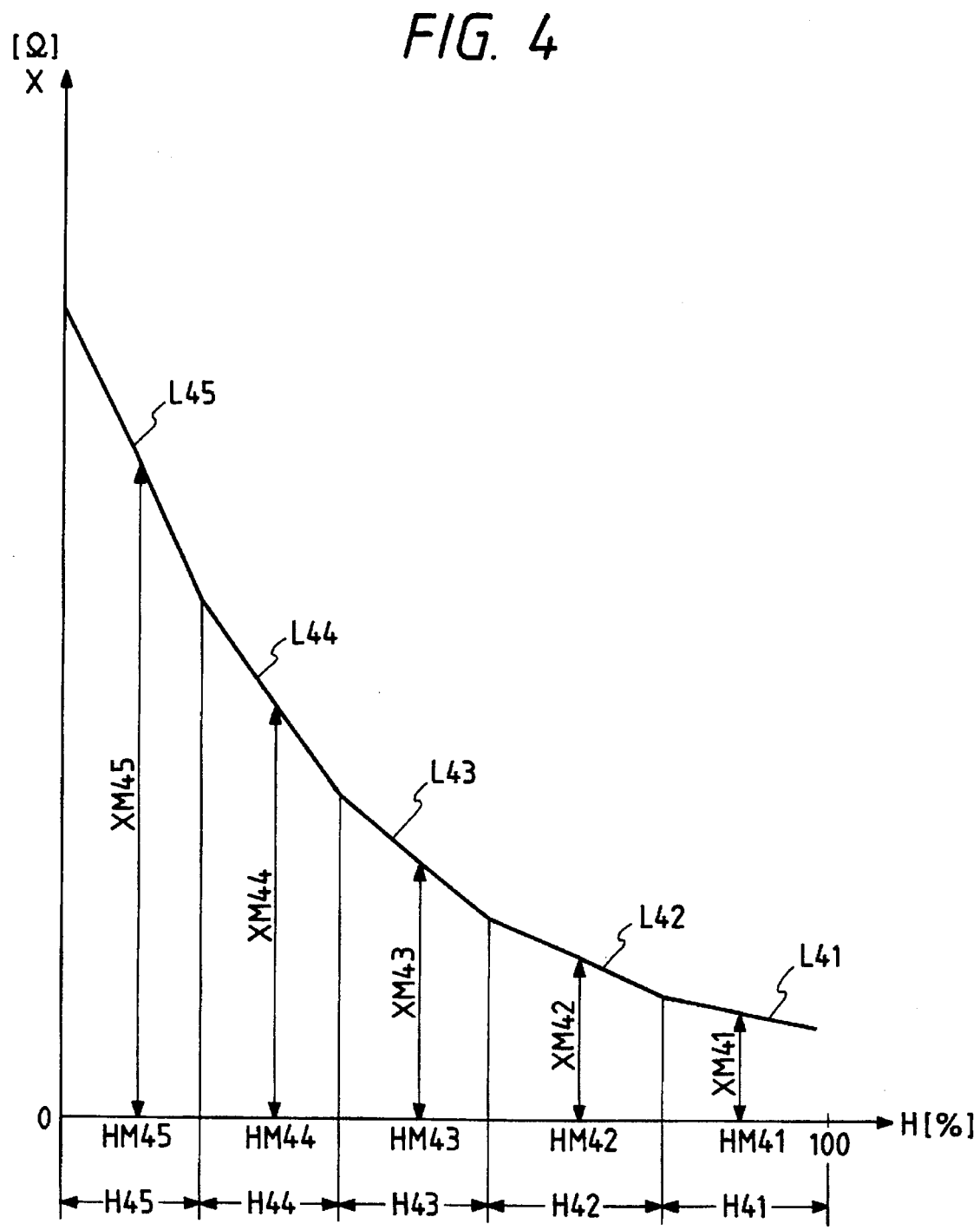
FIG. 4 is a graph approximating the characteristic curve of FIG. 2 with a plurality of straight lines.

FIG. 1 is a circuit configuration diagram of a humidity measuring apparatus according to an embodiment of the present invention. The element 1 is an oscillation circuit for generating an oscillation with a stable amplitude at an oscillation frequency selected as a specific frequency from 100 Hz to 10 kHz in accordance with the characteristics of a humidity sensor 2. Sensor 2 is the humidity sensor having the resistance varied with the temperature and humidity as indicated in the output characteristic curves of FIG. 2, for example, a high-molecular type ceramic sensor. R1 to R5 are reference resistors for use in making the linear approximation of the output characteristic curve of the humidity sensor 2 by dividing it into five regions as shown in FIG. 4, those resistors being connected to respective electronic switches SW1 to SW5 for switching the conductive state. C1 is a condenser for the AC coupling having such a value that the impedance of the oscillation circuit 1 at an oscillation frequency can be ignored with respect to the humidity sensor 2 or reference resistors R1 to R5. The element 3 is an AC amplifier for amplifying the output from the humidity sensor 2 and the reference resistors R1 to R5. The element 4 is a wave detection circuit for converting the AC signal amplified in the AC amplifier 3 to the DC signal. The element 5 is an A/D converter for converting the DC signal converted into the DC form in the wave detection circuit 4 into a digital value. The element 6 is a CPU for use in measuring the humidity by making the linear approximation for the output characteristic curve of the humidity sensor 2 based on the digital value input from the A/D converter 5. The CPU 6 controls the switching of the electronic switches SW1 to SW5. The element 7 is a thermistor (temperature sensor) having the resistance varied with the temperature, which is disposed near the humidity sensor 2. The element 8 is a reference power source for applying a reference voltage VR via a resistor 10 to the thermistor 7, and 9 is a DC amplifier for amplifying the output of the thermistor 7, the DC signal amplified by the DC amplifier 9 being output to the A/D converter 5.

Figure 3A:
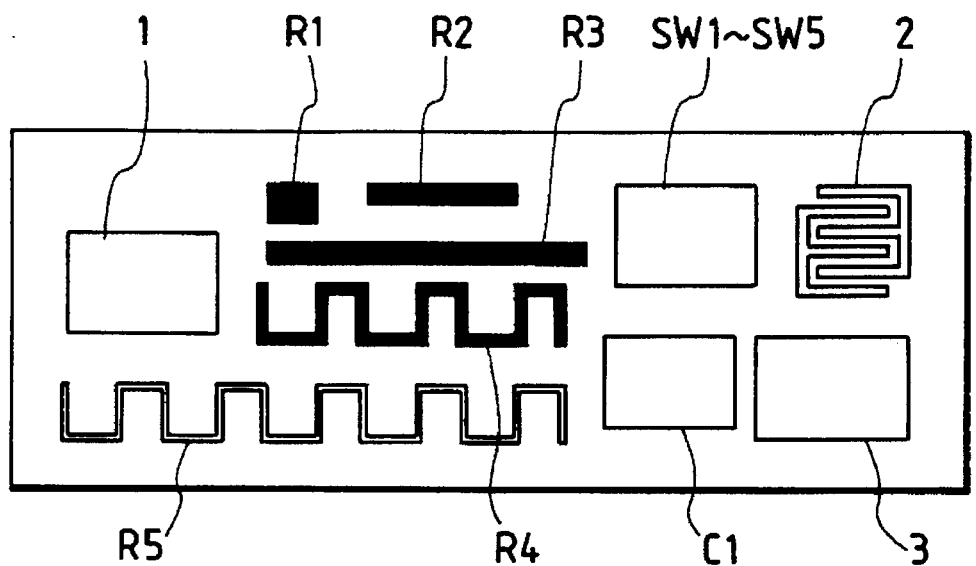
FIGS. 3A and 3B are views showing a substrate with the circuit packaged.
Figure 3B:
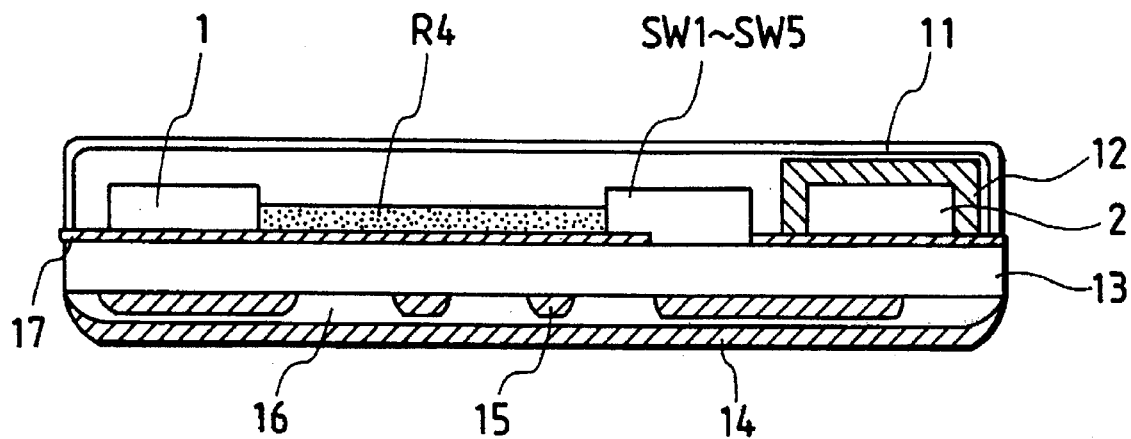

FIG. 3A is a plan view of a substrate having the circuits including the oscillation circuit 1, the humidity sensor 2 and the AC amplifier 3 as shown in FIG. 1 packaged therein, and FIG. 3B is a cross-sectional view of the substrate. On the ceramic substrate 13, there are printed the humidity sensor 2, the reference resistors R1 to R5, and the circuit electrodes 15, 17, onto which the electronic switches SW1 to SW5, the AC coupling condenser C1, and the AC amplifier 3 are soldered by the reflow method. An upper portion of the humidity sensor 2 is covered with a dust protective filter 12, and further a front surface of the ceramic substrate 13 is entirely covered with a shield plate 11 of metallic mesh. A back surface of the ceramic substrate 13 is printed with a shield electrode 14 via an insulation layer 16.

With the above configuration, the partial pressure ratio (output of the humidity sensor 2) between the reference resistors R1 to R5 and the humidity sensor 2 is input via the AC amplifier 3, the detection circuit 4 and the A/D converter 5 into the CPU 6, which reads out the resistance corresponding to the partial pressure ratio between the reference resistors R1 to R5 and the humidity sensor 2 from a table stored in the CPU 6 so as to calculate the resistance of the humidity sensor 2. On the other hand, the partial pressure ratio (output of the thermistor 7) between the resistor 10 and the thermistor 7 is input via the A/D converter 5 into the CPU 6, which reads out the temperature corresponding to the partial pressure ratio between the resistor 10 and the thermistor 7 so as to calculate the ambient temperature of the humidity sensor 2. The CPU 6 calculates the humidity from the resistance of the humidity sensor 2 and the ambient temperature of the humidity sensor 2.

Figure 2:
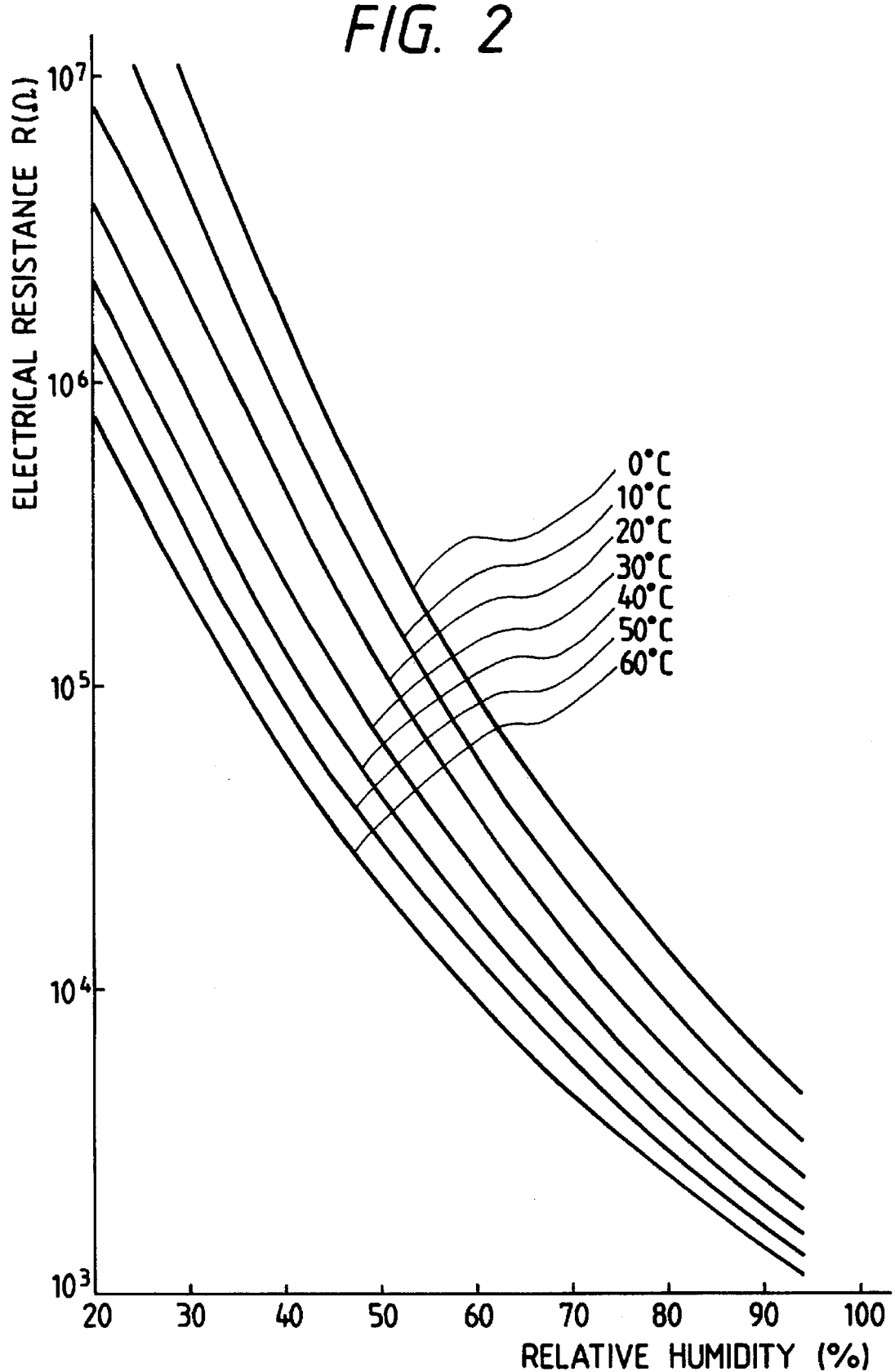
FIG. 2 is a graph representing the humidity-resistance characteristics of a humidity sensor.

FIG. 4 is a graph representing the linear approximation for the output characteristic curve of the humidity sensor 2 as shown in FIG. 2 by dividing it into five regions. X is a resistance of the humidity sensor 2, and H is a humidity corresponding to the resistance X of the humidity sensor 2. L41 is an approximate line when only the reference resistor R1 is in conduction by turning on the electronic switch SW1 only. H41 indicates the approximating range for the approximate line L41. XM41 is a resistance of the humidity sensor 2 at a humidity HM41 intermediate of the range H41. In the approximate line L41, when the temperature is T[° C.] and the resistance of the humidity sensor 2 is X[Ω], the humidity H[%] can be expressed as, $$H = A1(T) \cdot X + B1(T)$$

$$A1(T) = C1 \cdot T + D1 \text{ and}$$

$$B1(T) = E1 \cdot T + F1$$

Where C1, D1, E1, and F1 are line parameters for the approximate line L41 which are prestored in the CPU 6.

That is, the CPU can calculate the humidity H from the partial pressure ratio between the resistor 10 and the thermistor 7, i.e., the ambient temperature T of the humidity sensor 2, the partial pressure ratio between the reference resistor 1 and the humidity sensor 2, i.e., the resistance X of the humidity sensor 2, and the line parameters C1, D1, E1, F1 of the approximate line L41. For the other approximate lines L42 to L45, the CPU 6 can also calculate the humidity H from similar line parameters stored therein.

Figure 5:
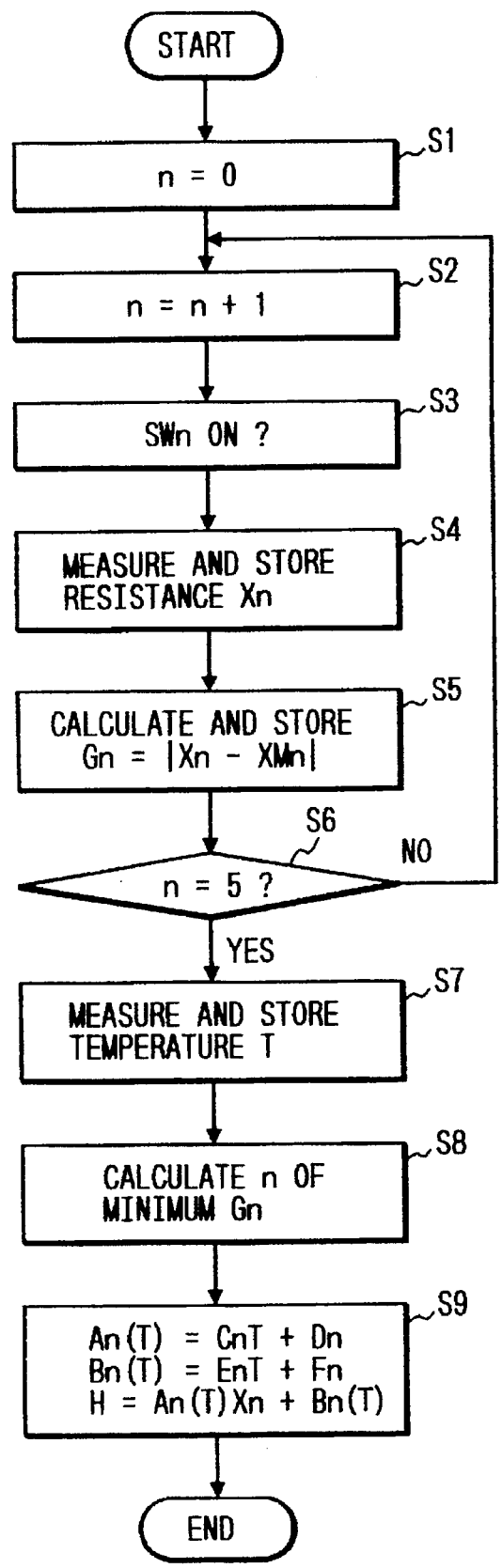
FIG. 5 is a flowchart showing the flow for measuring the humidity with the humidity measuring apparatus of FIG. 1.

Referring now to a flowchart of FIG. 5, the method of calculating the humidity with the CPU 6 will be described. First, a variable n is initialized (n=0) (step S1), the variable n is incremented by 1 (n=1) (step S2), and the electronic switch SWn (SW1) is turned on to allow the reference resistor R1 to conduct (step S3). And the resistance Xn (X1) of the humidity sensor 2 is calculated from the partial pressure ratio between the reference resistor Rn (R1) and the humidity sensor 2 input via the A/D converter 5, and then stored (step S4). The absolute value Gn (G1) of the difference between the resistance XMn (XM1) of the humidity sensor 2 at a humidity HMn (HM1) intermediate of the line approximate range Hn (Y1) prestored in the CPU 6 and Xn (X1) is calculated and stored (step S5). The above-described steps S2 to S5 are repeated five times (n=2 to 5) (step S6). Thereafter, the temperature of the thermistor 7, i.e., the ambient temperature T of the humidity sensor 2 is calculated from the partial pressure ratio between the resistor 10 and the thermistor 7 input from the A/D converter 5 (step S7). And the minimum n among G1 to G5 calculated at step S5 is calculated (step S8). The line parameters Cn, Dn, En, Fn corresponding to the value of n are read out from the CPU 6 to calculate An(T) and Bn(T) from the temperature T, and then the humidity H from An(T), Bn(T) and the resistance Xn (step S9), and thus the routine is terminated.

In this way, the output of the measuring element having the curve characteristic can be approximated by a plurality of approximate lines, so that the humidity measurement is allowed at high precision in a wide range.

EMBODIMENT 2

Figure 6:
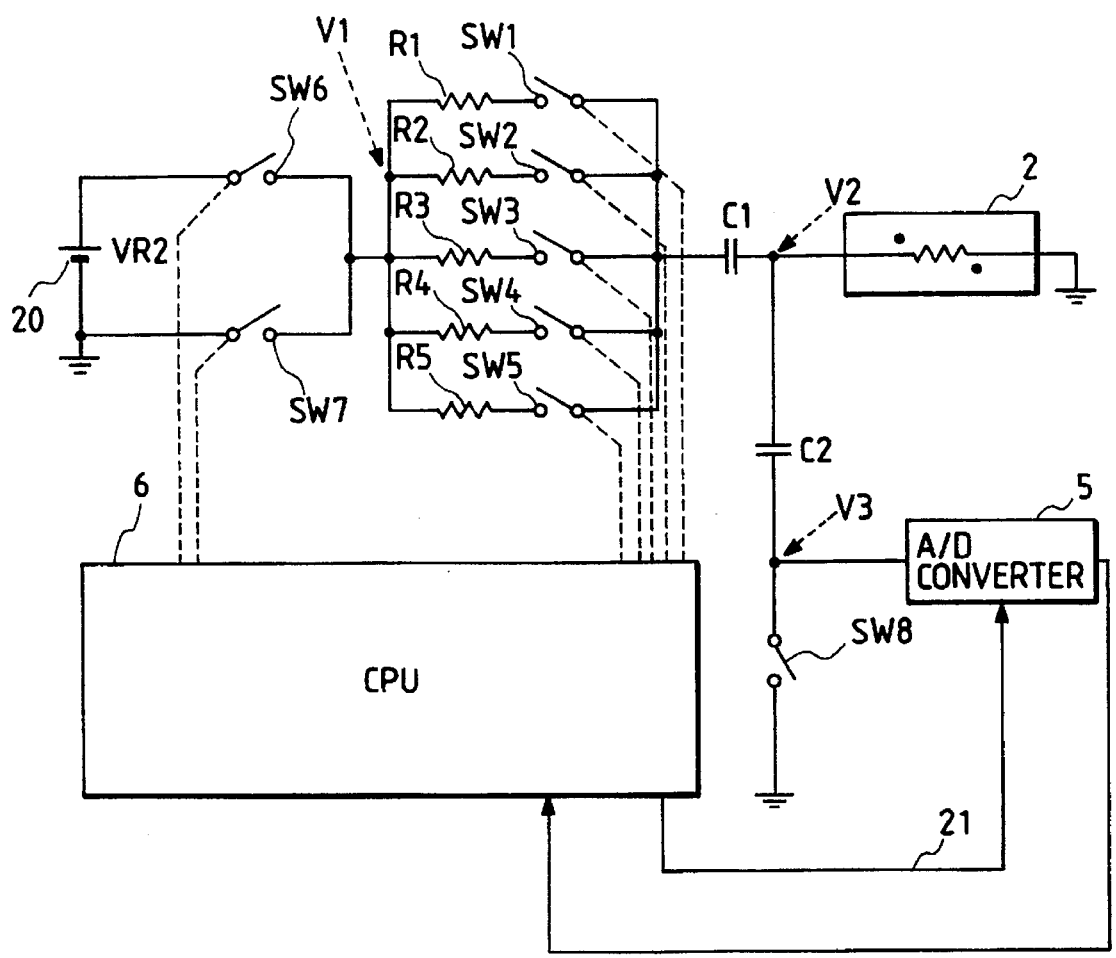
FIG. 6 is a circuit configuration diagram of a humidity measuring apparatus according to another embodiment of the present invention.

FIG. 6 is a circuit configuration diagram of a humidity measuring apparatus according to a second embodiment of the present invention. This embodiment is the circuit configuration according to the embodiment 1 as shown in FIG. 1 is simplified. Reference resistors R1 to R5, a coupling condenser C1, and a humidity sensor 2 are identical to those as shown in FIG. 1, and the explanation thereof will be omitted. The element 20 is a reference power source for applying a reference voltage VR2 to the humidity sensor 2. SW6 and SW7 are electronic switches to supply a bias voltage to the humidity sensor 2 by switching alternately between the reference voltage VR2 and the ground. C2 is a coupling condenser, and SW8 is an analog switch of the CMOS type, constituting a clamp circuit for the DC restoration to input the AC output V2 of the humidity sensor 2 to an A/D converter 5. A/D converter 5 is of the CMOS type, which outputs a digital value converted at that time to digital form to the CPU 6 if an A/D strobe 21 is input from the CPU 6.

Figure 7:
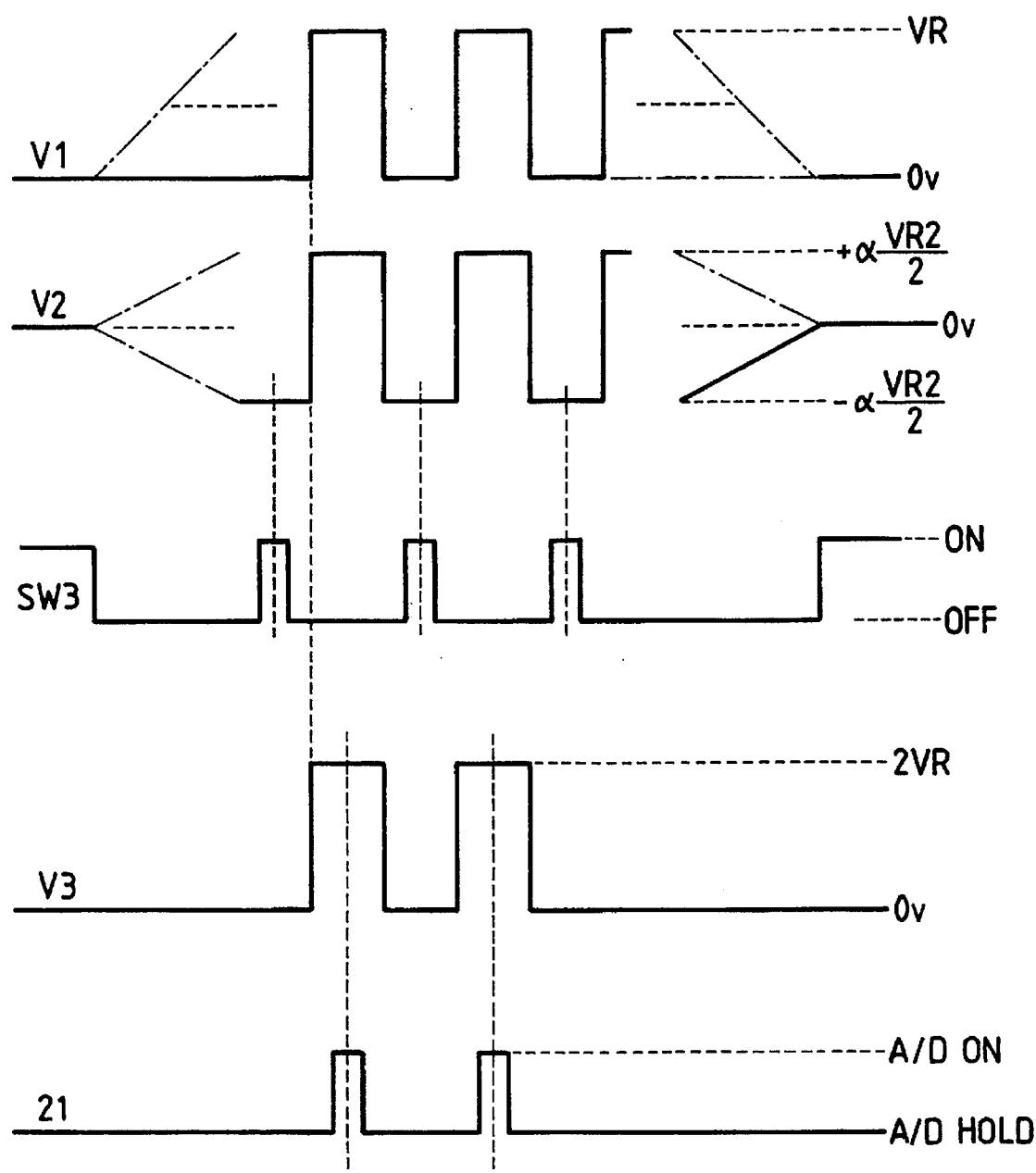
FIG. 7 are voltage waveform of various portions in the humidity measuring apparatus of FIG. 6.

Referring now to FIG. 7 illustrating the voltage waveforms, the operation will be described. The CPU 6 generates a timing signal having a frequency close to an optimal drive frequency (e.g., 1 KHz) of the humidity sensor 2 with a hardware timer or a software timer provided within the CPU 6, and switches alternately SW6 and SW7 to conduct in accordance with the timing signal. Thereby, the reference voltage VR2 and the ground are alternately applied to the reference resistors R1 to R5 as a bias voltage. The pulse signal having an amplitude VR is applied to the reference resistors R1 to R5 as indicated by V1 in FIG. 7. The pulse signal is applied via the reference resistors R1 to R5 and the AC coupling condenser C1 to the humidity sensor 2, to which an AC signal is then applied having a maximum of $+\alpha \cdot VR2/2$, a minimum of $-\alpha \cdot VR2/2$, and an amplitude of $\alpha \cdot VR2$, as indicated by V2 in FIG. 7. It is noted that $\alpha$ can be expressed as follows.

$$\alpha = Xn/(R1 + Xn)$$

The output of the humidity sensor 2 is DC restored by the coupling condenser C2 and the electronic switch SW8. That is, the CPU 6 turns on the SW3 when the humidity measurement is not made, while the CPU 6 turns it on at predetermined timings during the low level period of V1 and V2 and turns it off during other period, when the humidity measurement is made, as indicated by SW3 in FIG. 7. The A/D converter 5 is a CMOS type having a very high input impedance, so that the electric charge of C2 will not change. Therefore, to the input of the A/D converter 5, the positive pulse V3 is DC restored with the reference to 0-volt while the amplitude $\alpha \cdot VR2$ of V2 is held, as indicated by V3 in FIG. 7.

The CPU 6 supplies an A/D strobe 21 to the A/D converter 5 in synchronism with a positive peak period of the positive pulse V3 output from the coupling condenser C2 to convert a peak value of this positive pulse V3 into digital value which is then read by the CPU 6. In this way, the resistance X of the humidity sensor 2 can be calculated based on the digital value of the output of the humidity sensor 2.

And the CPU 6 calculates the ambient temperature T of the humidity sensor 2 based on the output of the thermistor 7, and calculates the humidity H from the resistance X, the temperature T and the line parameters as described in the embodiment 1.

As above described, it is possible to provide a simplified humidity measuring apparatus by eliminating the oscillation circuit 1, the AC amplifier 3, the wave detection circuit 4 which were required in the embodiment 1. Since the reference voltage VR2 and the ground are switched to be applied to the reference resistors R1 to R5, instead of using the oscillation circuit 1 with the output amplitude stabilized, to raise the measurement precision, it is possible to apply the signal having the stable amplitude. Also, there is no necessity of adjusting the amplitude at the input portion of the A/D converter 5, and thus suppressing the dispersion factor by making each circuit highly precise. Also, the signal processing at high precision such as the oscillation circuit 1 is eliminated, so that the cost reduction is realized.

EMBODIMENT 3

While the aforementioned embodiment 1 and embodiment 2 were such that the CPU 6 calculates the resistance of humidity sensor 2 from the output voltage of humidity sensor 2 and calculates the humidity based on the relation curve between the resistance and the humidity of humidity sensor 2, this embodiment is such that the CPU 6 calculates the humidity based on the relation curve between the output voltage and the humidity of humidity sensor 2 by inputting the output voltage V3 of humidity sensor 2 in the same circuit configuration (FIG. 6) as that of the humidity measuring apparatus in the embodiment 2.

Figure 8:
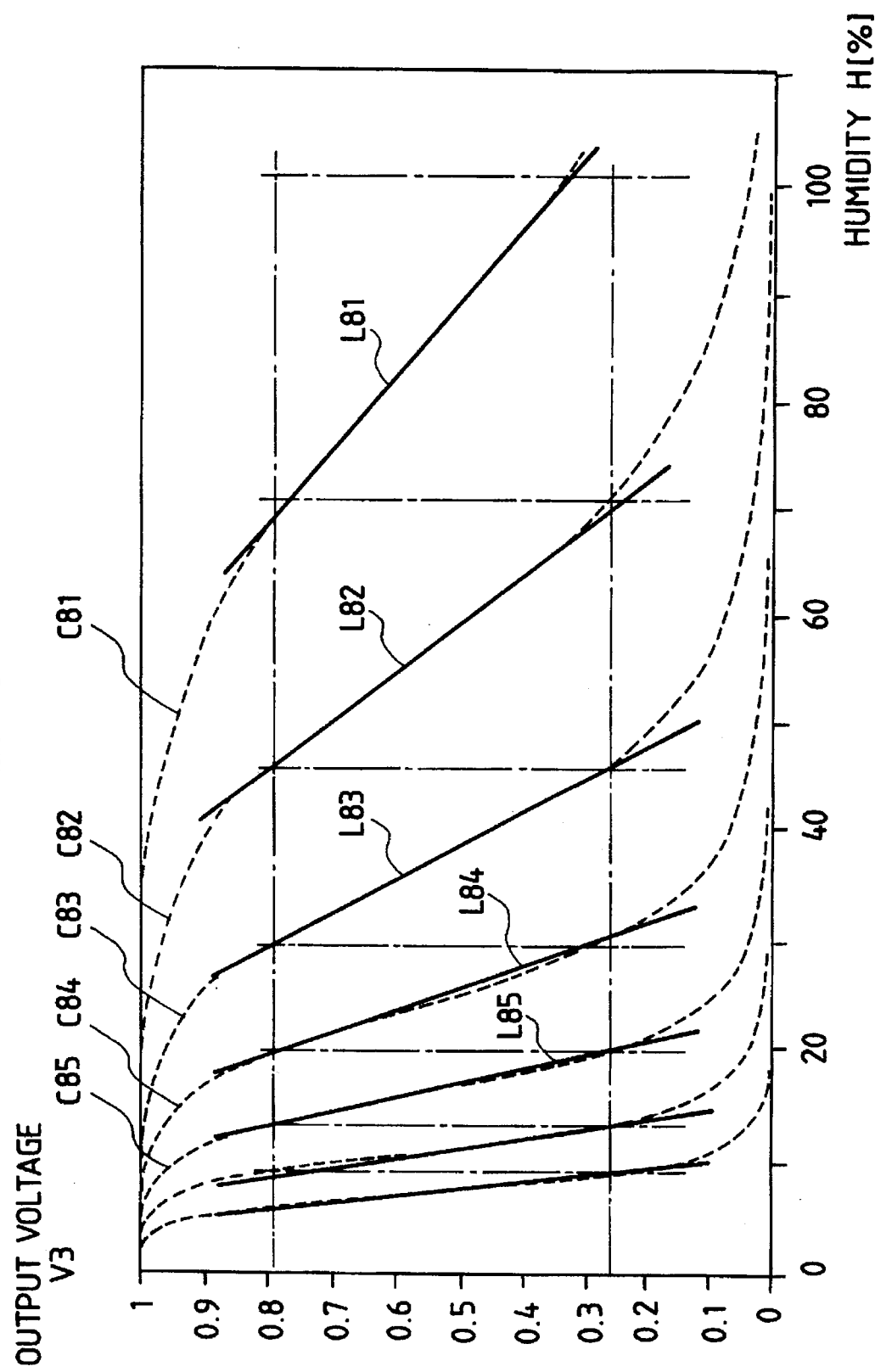
FIG. 8 is a graph showing the humidity-output voltage characteristic of the humidity sensor.

FIG. 8 is a graph representing the relation between the output voltage V3 and the humidity of humidity sensor 2. Dotted lines C81 to C85 in FIG. 8 are curves when reference resistors R1 to R5 are allowed to conduct by turning on electronic switches SW1 to SW5, respectively. Solid lines L81 to L85 superposed on the curves C81 to C85 are approximate lines. An approximate line L81 can be expressed by $$V3 = I1 \cdot H + J1$$

using parameters I1, J1. The approximate lines L82 to L85 can be expressed likewise using parameters I2 to I5 and J2 to J5. The CPU 6 prestores the parameters I1 to I5 and J1 to J5, and can calculate the humidity H by inputting the output voltage V3 of humidity sensor 2. As indicated within the dashed lines in FIG. 8, it is possible to calculate the humidity ranging from 15% to 100% by switching the reference resistors R1 to R5.

Figure 9:
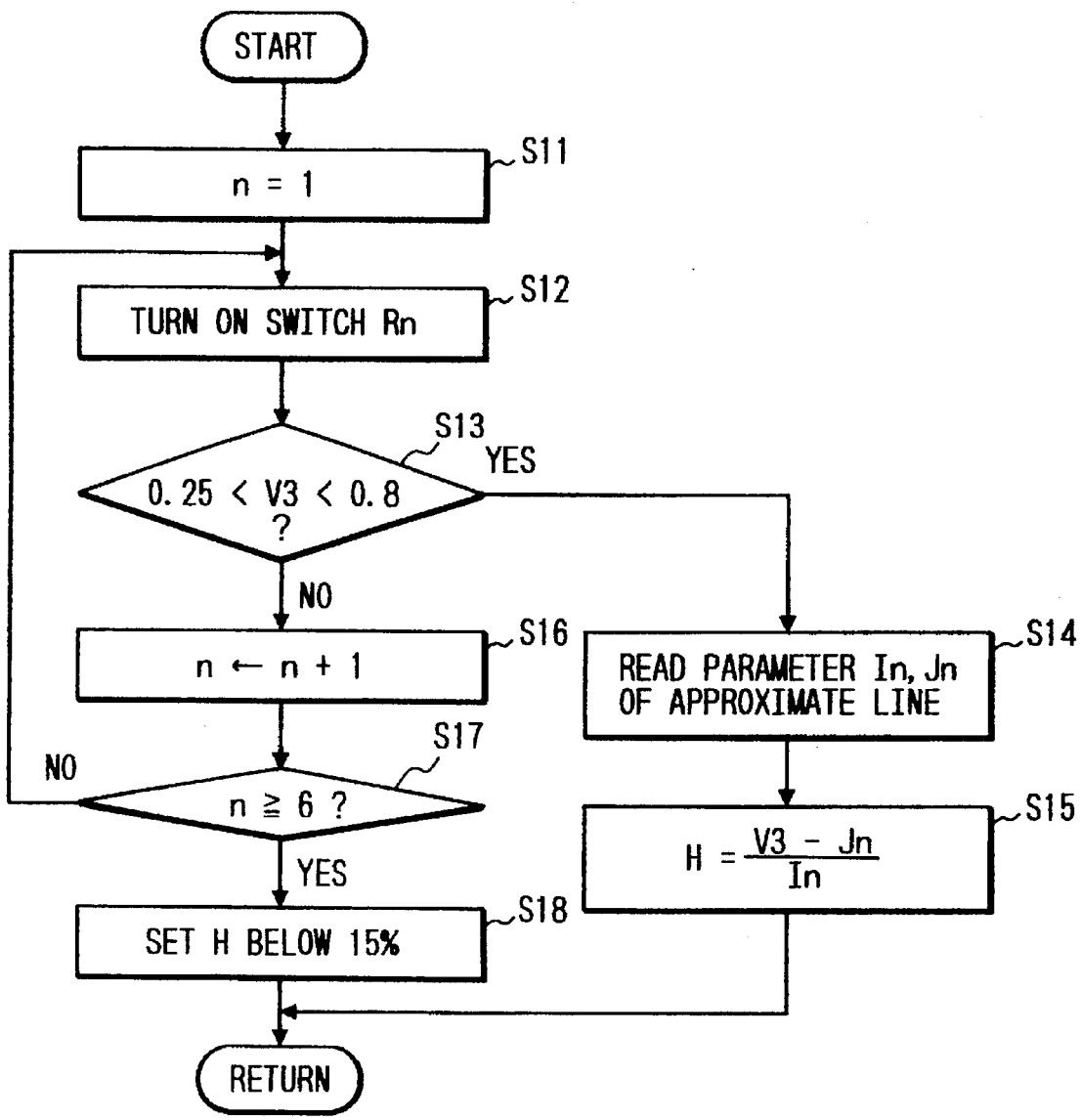
FIG. 9 is a flowchart showing the flow for measuring the humidity with the humidity measuring apparatus of FIG. 6.

FIG. 9 is a flowchart for calculating the humidity with the CPU 6. First, a variable n is 1 (step S11), a switch Sn is turned on to allow a reference resistor Rn to conduct, and the output voltage V3 of the humidity sensor 2 is input (step S12). And when the output voltage V3 is in a range from 0.25 to 0.8 (step S13), the parameters In, Jn of the approximate line for the reference resistor Rn are read out from the CPU 6 (step S14), and the humidity H is calculated (step S15). Also, at step S13, when the output voltage V3 is greater than or equal to 0.8, the content of the variable n is incremented by 1 (step S16), and if the content of variable n is smaller than 6, the routine proceeds to Step S12 (step S17). At step S17, if the content of variable n is greater than or equal to 6, the humidity is judged to be 15% or less (step S18), and the humidity calculation process is terminated.

It should be noted that if the number of reference resistors as shown in FIG. 6 is increased, the preciser humidity measurement for the humidity of 15% or less is permitted as shown in FIG. 8.

EMBODIMENT 4

Figure 10:
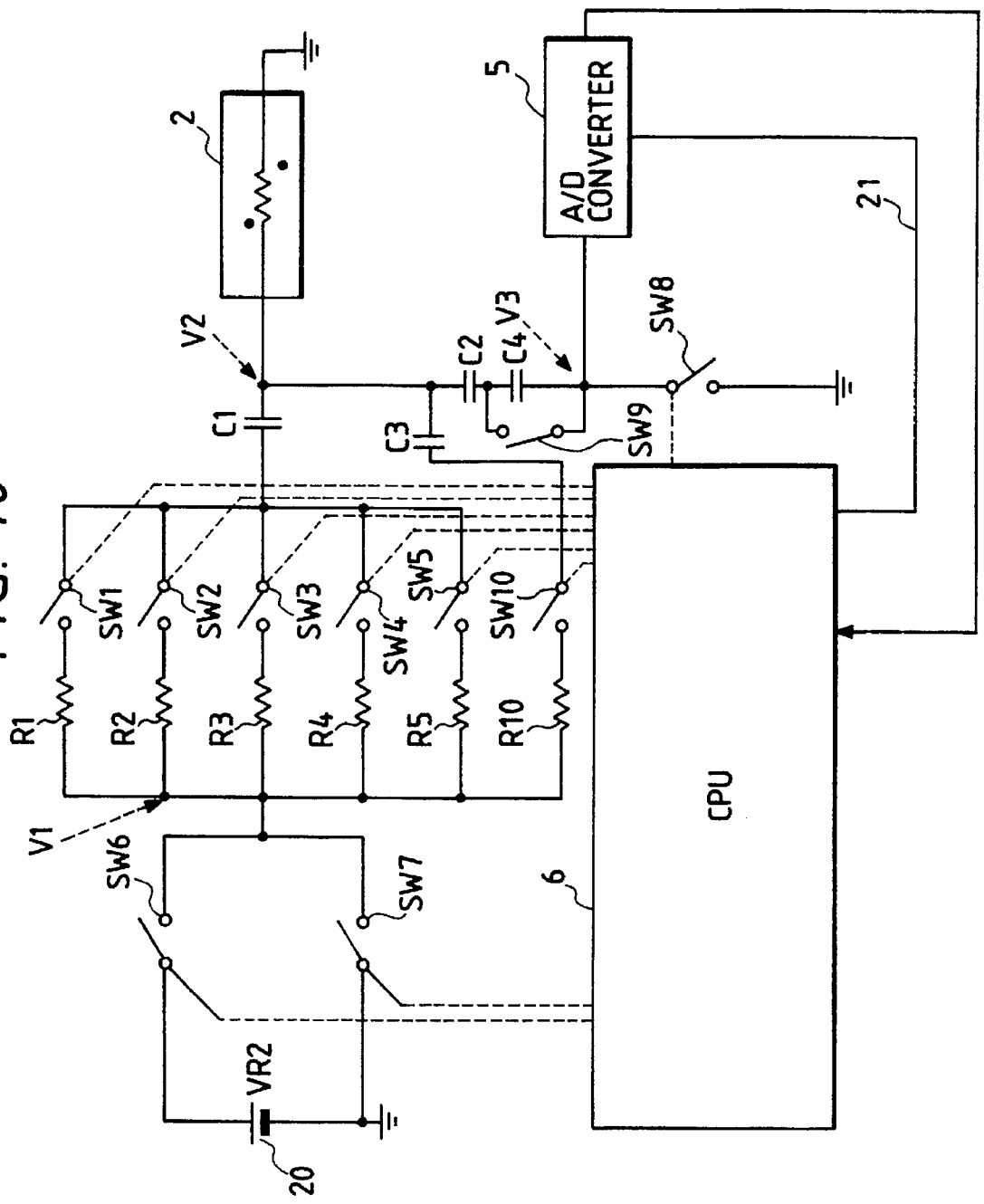
FIG. 10 is a circuit configuration diagram of a humidity measuring apparatus according to another embodiment of the present invention.

FIG. 10 is a circuit configuration diagram of a humidity measuring apparatus according to a fourth embodiment of the present invention. In the previous third embodiment, if the value of the humidity sensor 2 is 10 MΩ or greater, a measurement error may occur due to floating capacities present in the switches SW1 to SW5, a floating capacity C5 present in the humidity sensor 2, or floating capacities present in other circuits. This embodiment is to reduce such a measurement error caused by those floating capacities.

A humidity sensor 2, an A/D converter 5, a CPU 6, a reference power source 20, an A/D strobe 21, switches SW1 to SW8, and a coupling condenser C1 are the same as those of FIG. 6, and the explanation will be omitted. A resistor R10 is a reference resistor for enabling the measurement for a humidity of 10% to 15%, and SW10 is a switch for switching for conductive state of the reference resistor R10. C3 is a coupling condenser having a smaller capacity than the coupling condenser C1, and connected in series to the reference resistor R10. One end of the series circuit or one end of the condenser C3 is connected to a contact point of the condenser C1, the condenser C2, and the humidity sensor 2, and the other end of the series circuit or one end of the reference resistor R10 is connected to a contact point of SW6, SW7, and the reference resistors R1 to R5. A switch SW9 and a condenser C4 are connected in parallel, with its parallel circuit inserted in a connection of the condenser C2 and the switch SW8. A connection point between the switch SW8, the switch SW9 and the condenser C4 is connected to the A/D converter 5. It is noted that the values of C1, C2, C3, and C4 satisfy the relation, $$C2/C1 \cong (1/(1/C2+1/C4))/C3$$

The flow of calculating the humidity with the CPU 6 will be described below. The CPU 6 turns on the switch SW9, and make the same control as that of the embodiment 2 shown in FIG. 9. If it is found at step 8 that the voltage for permitting the linear approximation can not be obtained by the selection of reference resistors R1 to R5, the CPU 6 turns off the switches SW1 to SW5, turns on the switch SW10, and turns off the switch SW4. And it makes smaller the frequency of switching the switch SW6 and SW7. For example, the frequency is switched from 1 kHz to 50 Hz. And the CPU starts the clamp operation to read the value of V2 with the A/D conversion in the same way as in the embodiment 3. The frequency is reduced in inverse proportion to the time constant in the product of C1 and a resistor of humidity sensor. For example, when C1 is 0.3 μF, and the impedance of the humidity sensor 2 is 60 MΩ, the frequency is 50 Hz, and when C1 is 0.3 μF and the impedance of the humidity sensor 2 is 6 kΩ, the frequency is 500 Hz. The clamp timing for use is a timing as shown in FIG. 7, and when the drive frequency of VR2 is changed, the timing is adjusted in proportion to it, so that the same clamp operation as in FIG. 7 is conducted.

If the value of the humidity sensor 2 is 10 MΩ or greater, the approximation calculation is not allowed by a method of the embodiment 3 due to the existence of floating capacities present in the humidity sensor 2 and other circuits, but in this embodiment, when the resistance of the humidity sensor 2 is larger, the values of coupling condensers C3, C2, C4 and the drive frequency of a reference power source are changed in consideration of such floating capacities, so that a measurement error caused by such floating capacities can be reduced to make a correct measurement. Because the value of the condenser C3 is decreased, the time during which the condenser C3 gets to a stationary state in the clamp operation can be shortened, resulting in faster measurement.

EMBODIMENT 5

Figure 11:
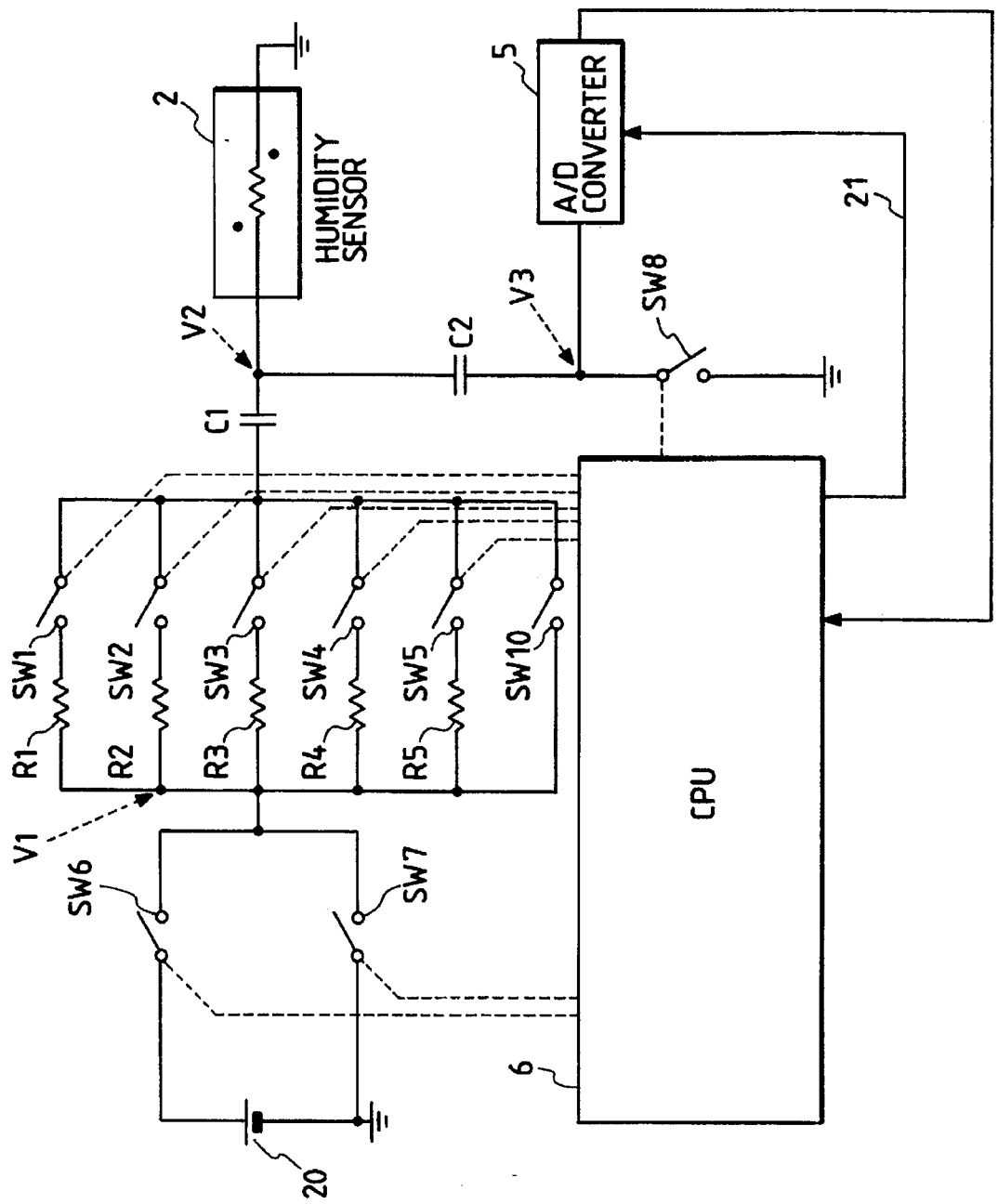
FIG. 11 is a circuit configuration diagram of a humidity measuring apparatus according to another embodiment of the present invention.

FIG. 11 is a circuit configuration diagram of a humidity measuring apparatus according to a fifth embodiment of the present invention. A humidity sensor 2, an A/D converter 5, a CPU 6, a reference power source 20, an A/D strobe 21, switches SW1 to SW8, and a coupling condenser C1 are the same as those of FIG. 6, and the explanation will be omitted. SW10 is a switch connected in parallel to a reference resistor R1 and a switch SW1. It is considered that this circuit is one in which a reference resistor having a resistance of 0Ω is connected in parallel to the reference resistors R1 to R5.

The flow of calculating the humidity with the CPU 6 will be described below. The CPU 6 makes the same control as that of the embodiment 2 shown in FIG. 9. If it is found at step 8 that the voltage for permitting the linear approximation can not be obtained by the selection of the reference resistors R1 to R5, the CPU 6 turns off the switches SW1 to SW5, and turns on the switch SW10. And the CPU 6 calculates the humidity by inputting the output voltage V3 of the humidity sensor 2 via the A/D converter 5.

In this way, when the humidity is low, or when the resistance of the humidity sensor 2 is high, the reference resistance is set at 0Ω by the switch SW10, so that the influence of the floating capacity present in the condenser C1 on the side of the reference resistors R1 to R5 can be reduced. Thereby, the output V2 of the humidity sensor 2 is unlikely to contain the noise, and the clamp output voltage V3 can be stabilized. Therefore, a stabler humidity measurement is allowed.

EMBODIMENT 6

Figure 12:
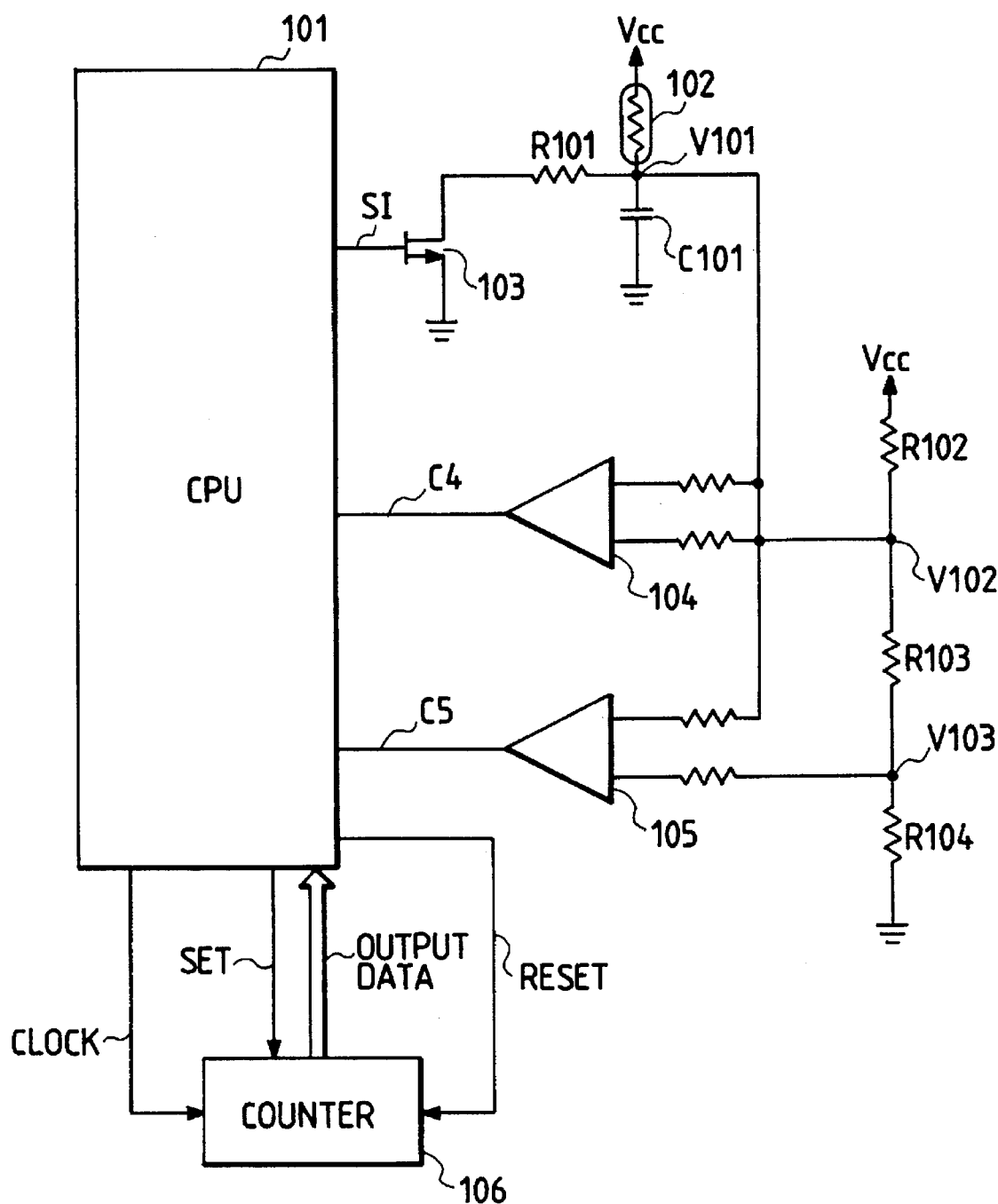
FIG. 12 is a circuit configuration diagram of a humidity measuring apparatus according to another embodiment of the present invention.

FIG. 12 is a circuit configuration diagram of a humidity measuring apparatus according to a sixth embodiment of the present invention. Element 101 is a microcomputer, element 102 is a humidity sensor having its resistance varied with the temperature and the humidity, for example, a high-molecular type ceramic sensor. Element 103 is an electronic switch, for which an open drain terminal of the output port of the microcomputer can be directly used. Elements 104, 105 are comparators for comparing the output voltage of the humidity sensor 102 with predetermined voltages V103, V102, and 106 is a counter for counting a predetermined time.

Figure 13:
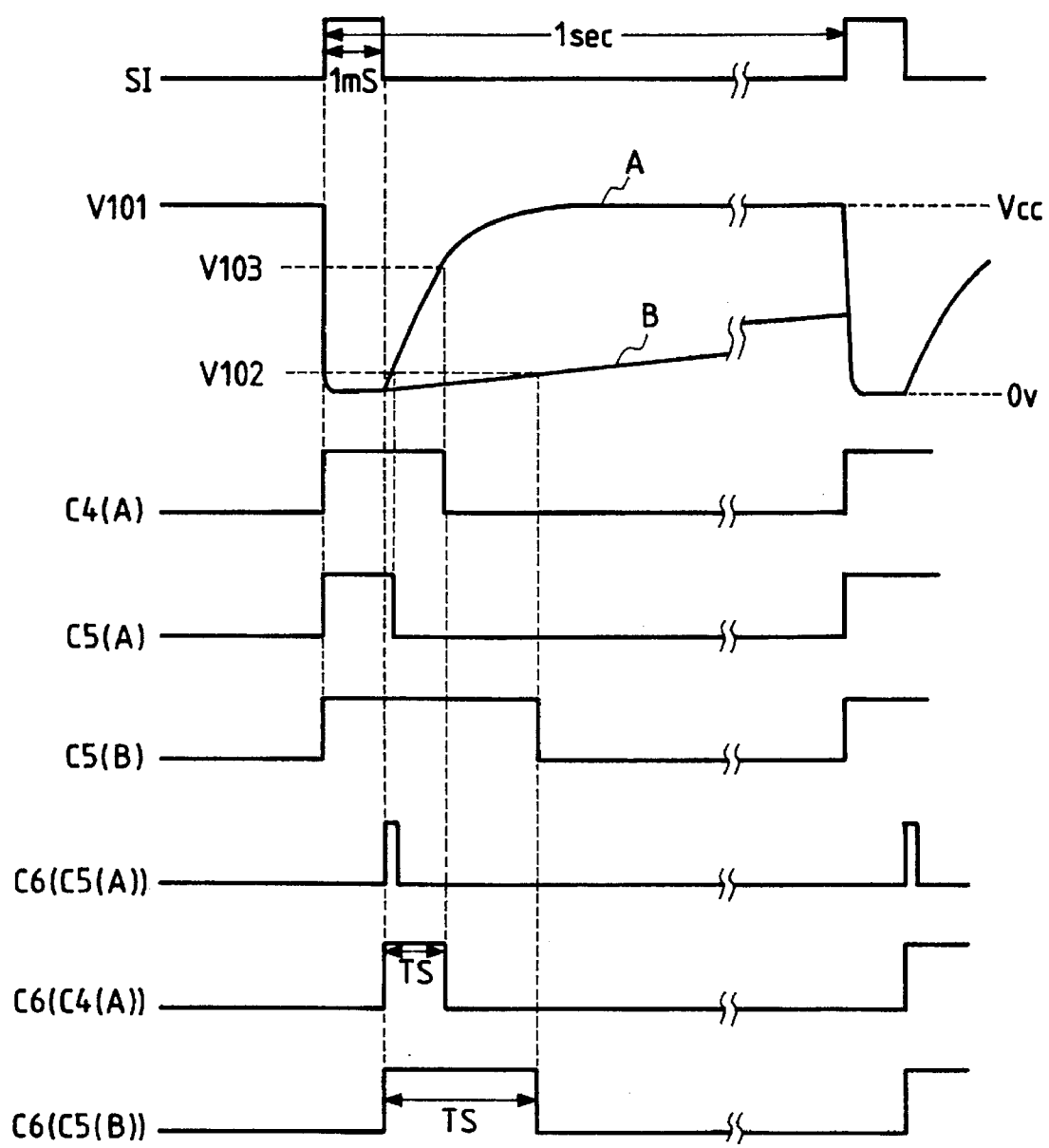
FIG. 13 is a voltage waveforms of various portions in the humidity measuring apparatus of FIG. 12.

FIG. 13 is a timing chart in the humidity measuring apparatus as shown in FIG. 12. SI in FIG. 13 is a control timing for the electronic switch 103, in which when the microcomputer 101 sets SI at a high level, the electronic switch 103 is allowed to conduct. The time for which SI is retained at the high level is set to be 1/1000 or less a period of SI1. With such a setting, after the electronic switch 103 is allowed to conduct to energize the humidity sensor 102, the next measurement can be conducted in a state where electrons or ions having travelled within the humidity sensor 102 have completely returned to their initial state. If SI rises up to make the electronic switch 103 conductive, electric charges of a condenser C101 charged are discharged, so that V101 is set at 0 V. And if SI is down at a low level, and the electronic switch is opened, the condenser C101 is charged via the humidity sensor 102, and V101 gradually increases to a saturated state. The larger the resistance of the humidity sensor 102, the longer the time required for V101 to reach the saturated state, while the smaller the resistance, the shorter the time required for V101 to reach the saturated state. Note that A indicates a high humidity and B a low humidity. C4, C5 are outputs from comparators 104, 105, respectively. C4 is at a high level when V101 is smaller than V103, and C5 is at a high level when V101 is smaller than V102. Note that (A) and (B) indicate the outputs of the comparator at the high humidity and the low humidity, respectively. C6 is a time chart representing the interval from the time at which SI is changed from high to low level until the time at which C4 (A) or C5 (B) is changed from high to low level.

The resistance of the humidity sensor 102 when the change of V101 is A in FIG. 13 can be obtained in the following way. The time TS indicated in C6 (C4(A)) is counted by the counter 106. From the time TS counted, the resistance RS of the humidity sensor 102 is obtained by the following expression.

$$RS=TS/(C1 \cdot \log(1/(1-V103/Vcc)))$$

As in the embodiment 1, the humidity is calculated from the resistance RS of the humidity sensor 102.

The resistance of the humidity sensor 102 when the change of V101 is B in FIG. 13 can be obtained likewise. Herein, the different point from A is that the time TS indicated in C6 (C5(B)) is counted, and the resistance RS of the humidity sensor 102 is calculated by the following expression.

$$RS=TS/(C1 \cdot \log(1/(1-V102/Vcc)))$$

In this way, the resistance of humidity sensor is obtained from the charging time in RC circuit, resulting in a simpler circuit configuration.

Figure 16:
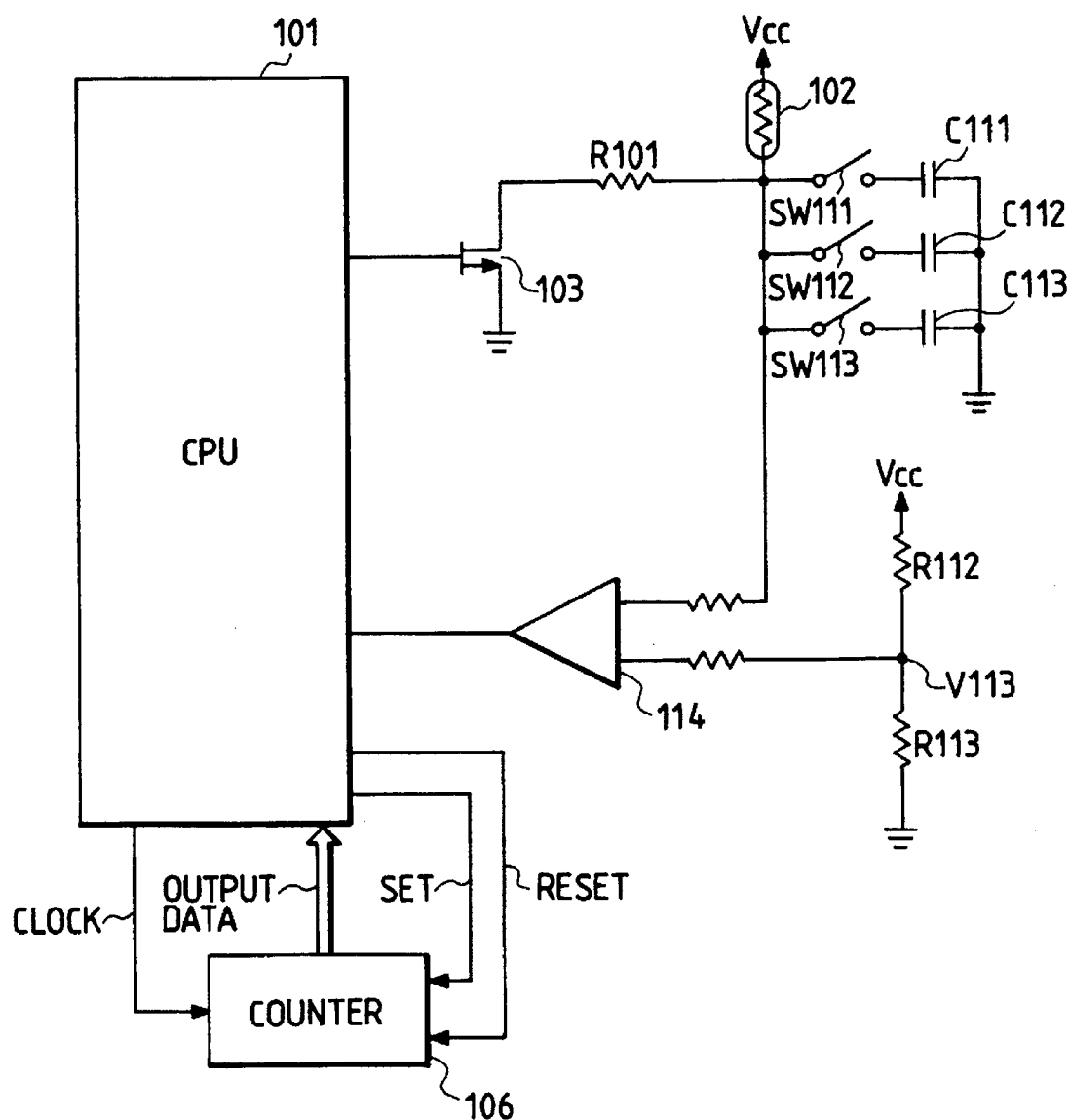
FIG. 16 is a circuit configuration diagram of a humidity measuring apparatus according to another embodiment of the present invention.

It should be noted that there are provided condensers C111, C112, C113 and switches SW111, SW112 and SW113, as shown in FIG. 16, and by switching them, the higher precision humidity measurement is allowed. Also, by setting V113 in the circuit of FIG. 16 in accordance with the following expression, the resistance of the humidity sensor 102 can be calculated without any logarithmic calculation.

$$V113=Vcc(1-1/e)=0.63 \cdot Vcc$$

Substituting this V113 into the previous expression of RS, $$RS=TS/C1$$

and it can be found that the resistance of the humidity sensor 102 can be calculated without any logarithmic calculation.

From the sensor resistance RS thus measured, the humidity H can be obtained as follows.

Figure 14:
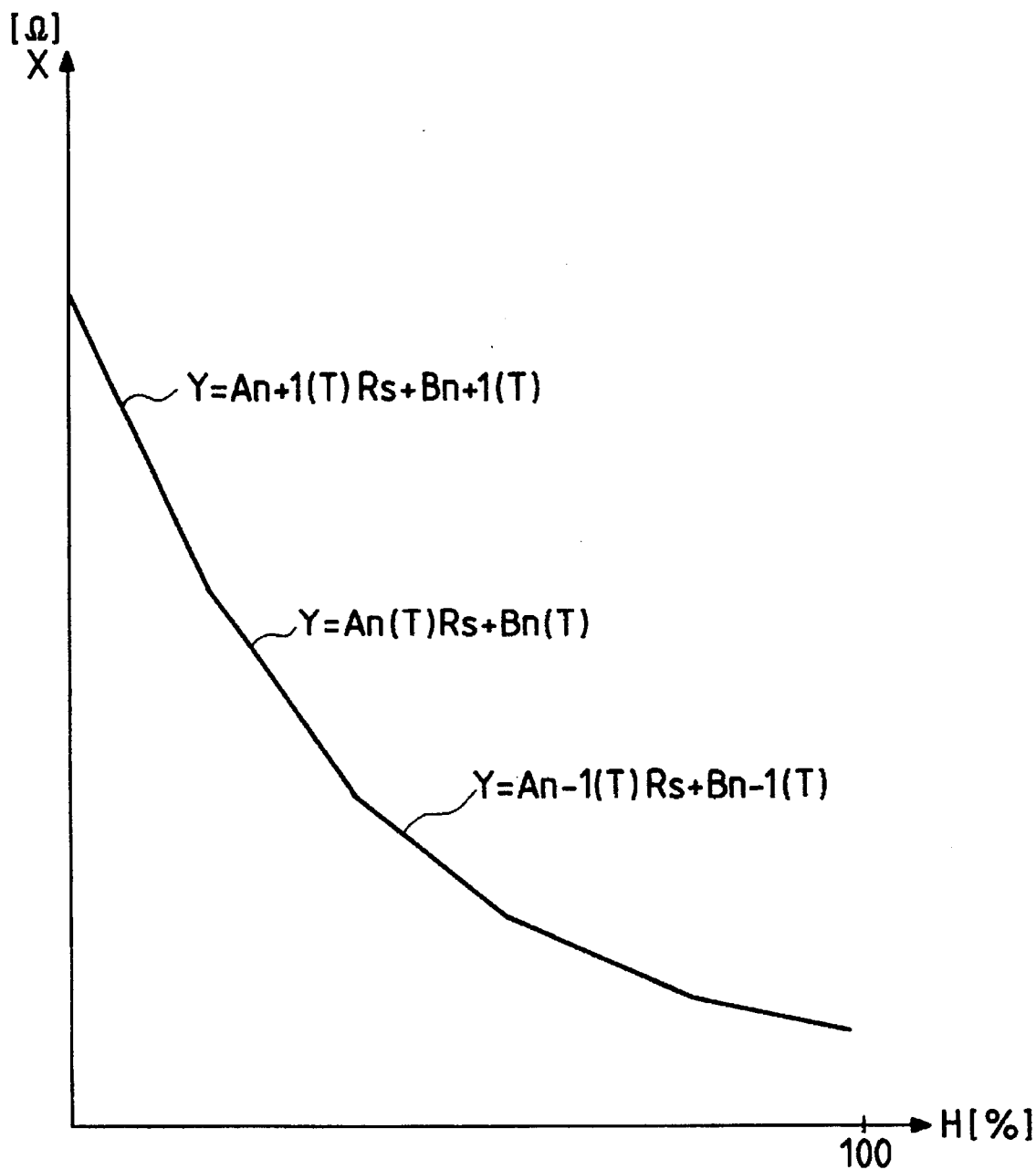
FIG. 14 is a graph approximating the characteristic curve of FIG. 2 with a plurality of straight lines.

The output curve of the sensor is linearly approximated by dividing it into five regions at each temperature T, as shown in FIG. 14. In accordance with a flowchart shown in FIG. 15, the flow of obtaining the humidity H will be described.

The linear approximate region is selected from RS and the ambient temperature T measured by a temperature sensor provided near the humidity sensor, and the line parameters Cn, Dn, En, Fn are obtained from a lookup table prestored in the CPU. AN(T) and BN(T) are obtained from RS, T, Cn, Dn, and En. And the humidity is obtained from AN(T), BN(T) thus obtained.

EMBODIMENT 7

Figure 17:
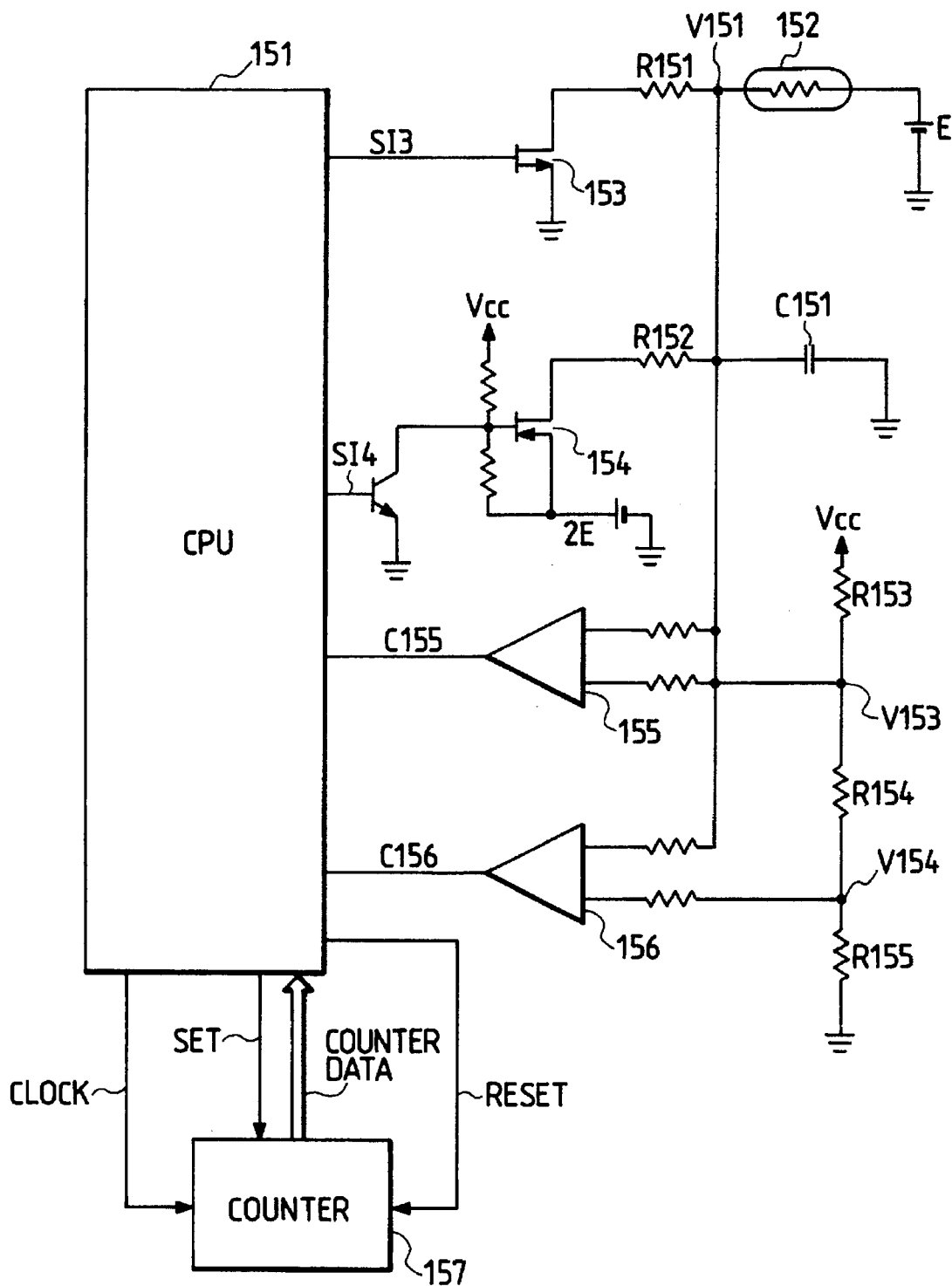
FIG. 17 is a circuit configuration diagram of a humidity measuring apparatus according to another embodiment of the present invention.
Figure 18:
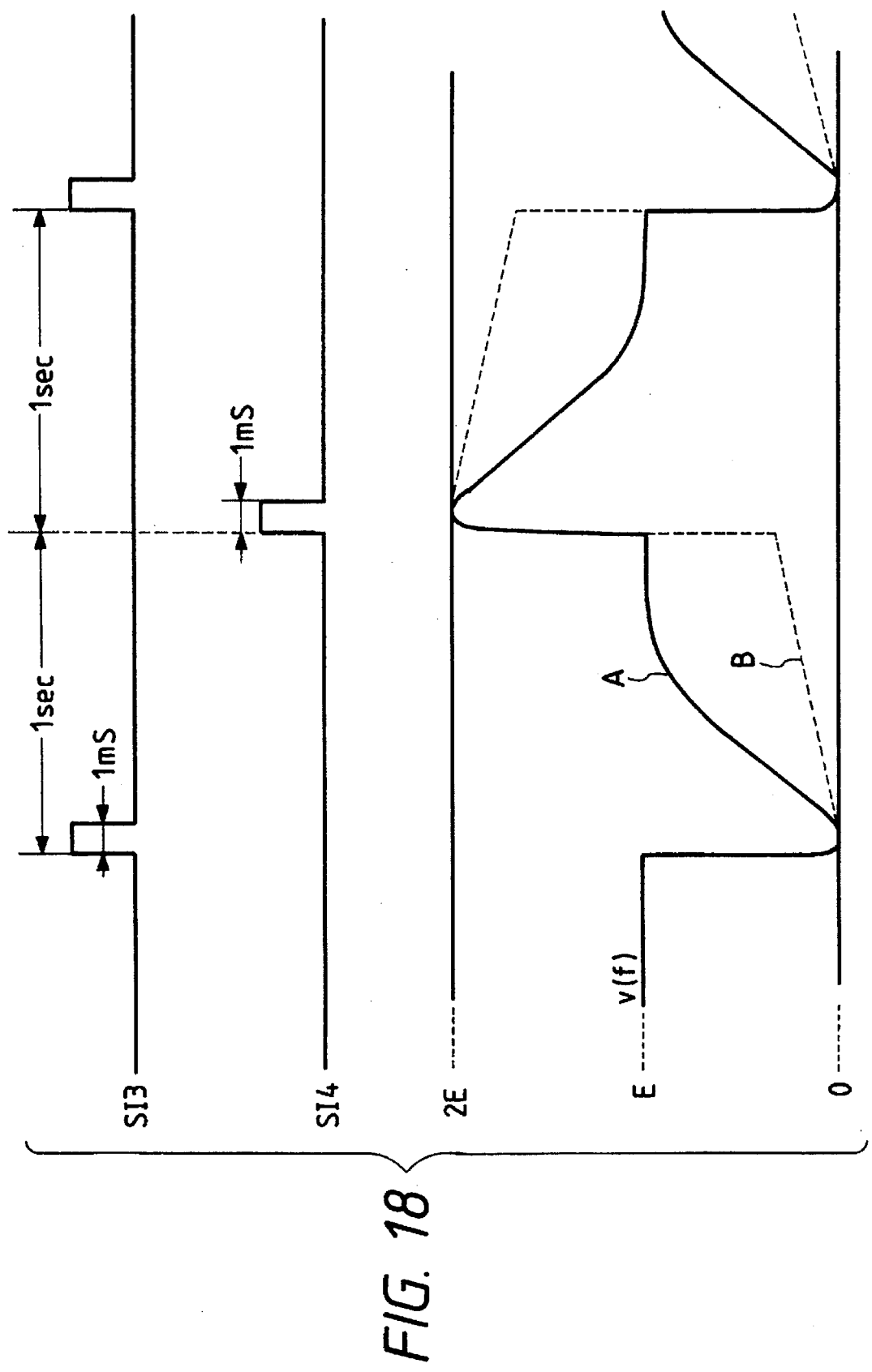
FIG. 18 is a diagram showing the waveforms of S13, S14 and V151 in the humidity measuring apparatus of FIG. 17.

FIG. 17 is a circuit configuration diagram of a humidity measuring apparatus according to a seventh embodiment of the present invention. Element 151 is a microcomputer and element 152 is a humidity sensor which may be a high-molecular type ceramic sensor, for example. The resistance of the humidity sensor 152 will vary with the temperature and the humidity as shown in FIG. 2. Elements 153, 154 are electronic switches for conducting the electric current to the humidity sensor 152 in making the measurement, for which an open drain terminal of the output port of the microcomputer 151 can be directly used. The time for which the electronic switches 153, 154 are in the on state is set to be no more than 1/1000 one period. With such a setting, electrons or ions having travelled within the humidity sensor 152 in the humidity measurement can be restored to the initial state. When the humidity measurement is not made, both the electronic switches 153, 154 are held in an open state, and a measurement condenser C151 is charged with electric charges corresponding to a voltage E(V). When the humidity measurement is made, two pulse waves (1 ms) as indicated by SI3, SI4 in FIG. 18 are generated alternately at a frequency of two seconds, respectively. Thus, the output voltage V151 of the humidity sensor 152 has a symmetrical waveform around E(V), as indicated by V151 in FIG. 18, so that the DC voltage applied to the humidity sensor 152 becomes zero. The resistance of the humidity sensor 152 is obtained by measuring the time for which the condenser C151 has been charged, starting from the rising of SI3 pulse.

Figure 19:
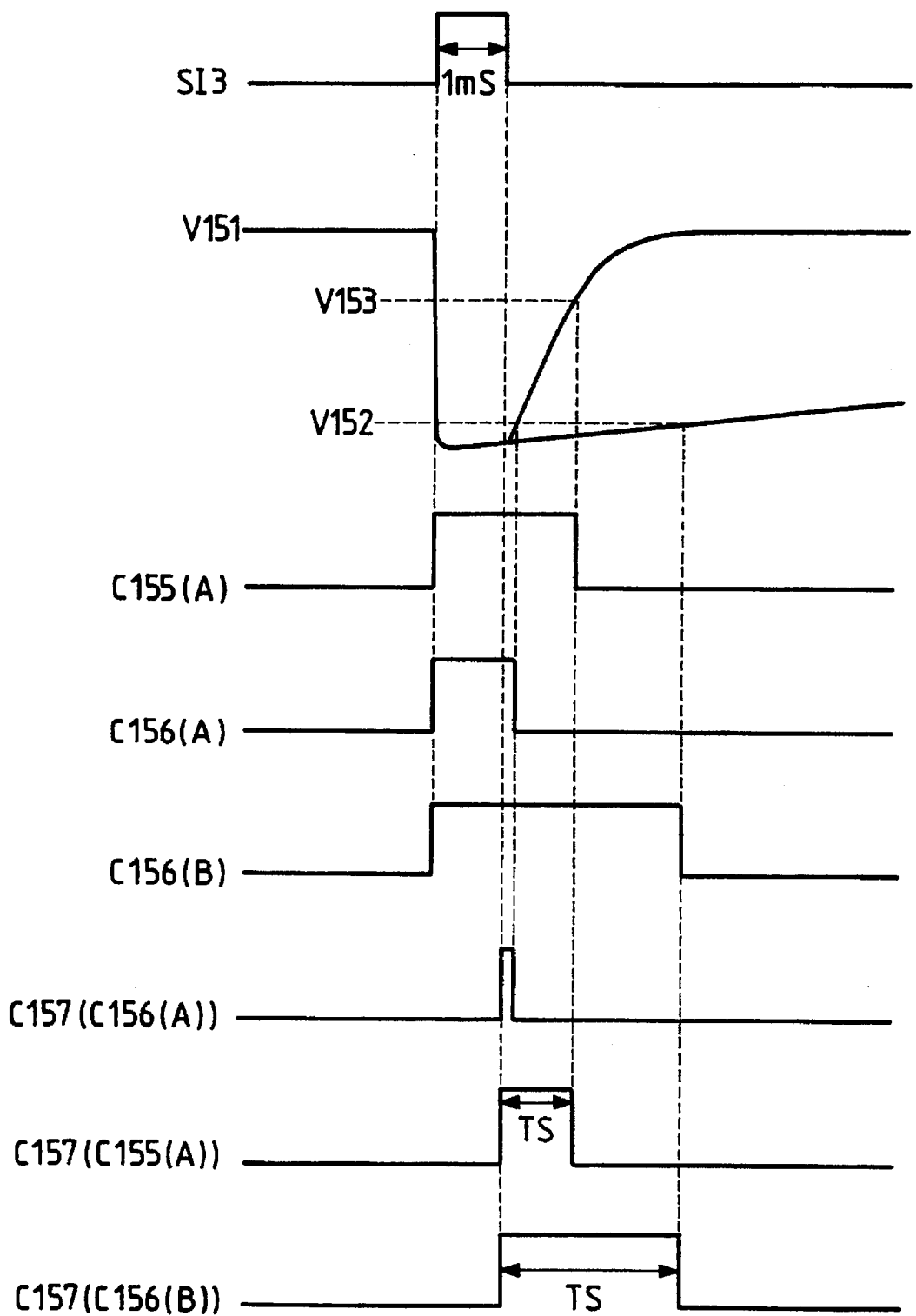
FIG. 19 is a diagram showing the waveforms of various portions in the humidity measuring apparatus of FIG. 17.

In measuring the humidity, the electronic switch SI3 is allowed to conduct, as indicated by SI3 in FIG. 19, so that electric charges of the condenser C151 which has been charged are rapidly discharged as indicated by V151 in FIG. 19. After the elapse of 1 ms, the electronic switch SI3 is opened, so that the condenser C151 is charged via the humidity sensor 152. And comparators 155, 156 compare a terminal voltage V151 of the condenser C151 which is being charged and threshold voltages V153, V154, respectively. And a counter 157 counts the interval TS from the time when the electronic switch SI3 is opened to the time when the threshold voltage V153, V154 is exceeded. At this time, since the comparators 155, 156 have their outputs reversed when V151 reaches the threshold voltages V153, V154, respectively, as indicated by C155, C156 in FIG. 19, the counter 157 counts correspondingly as indicated by C157 in FIG. 19. In FIG. 19, A indicates when the sensor resistance is small or the humidity is high, while B indicates when the sensor resistance is large or the humidity is low.

Substituting the time TS counted by the counter 157 into the following expression, the resistance of the humidity sensor can be calculated.

$$RS=TS/(C1 \cdot \log(1/(1-V3/E)))$$

And as in the previous embodiment, the humidity H is calculated from the resistance RS of the humidity sensor 152.

Figure 20:
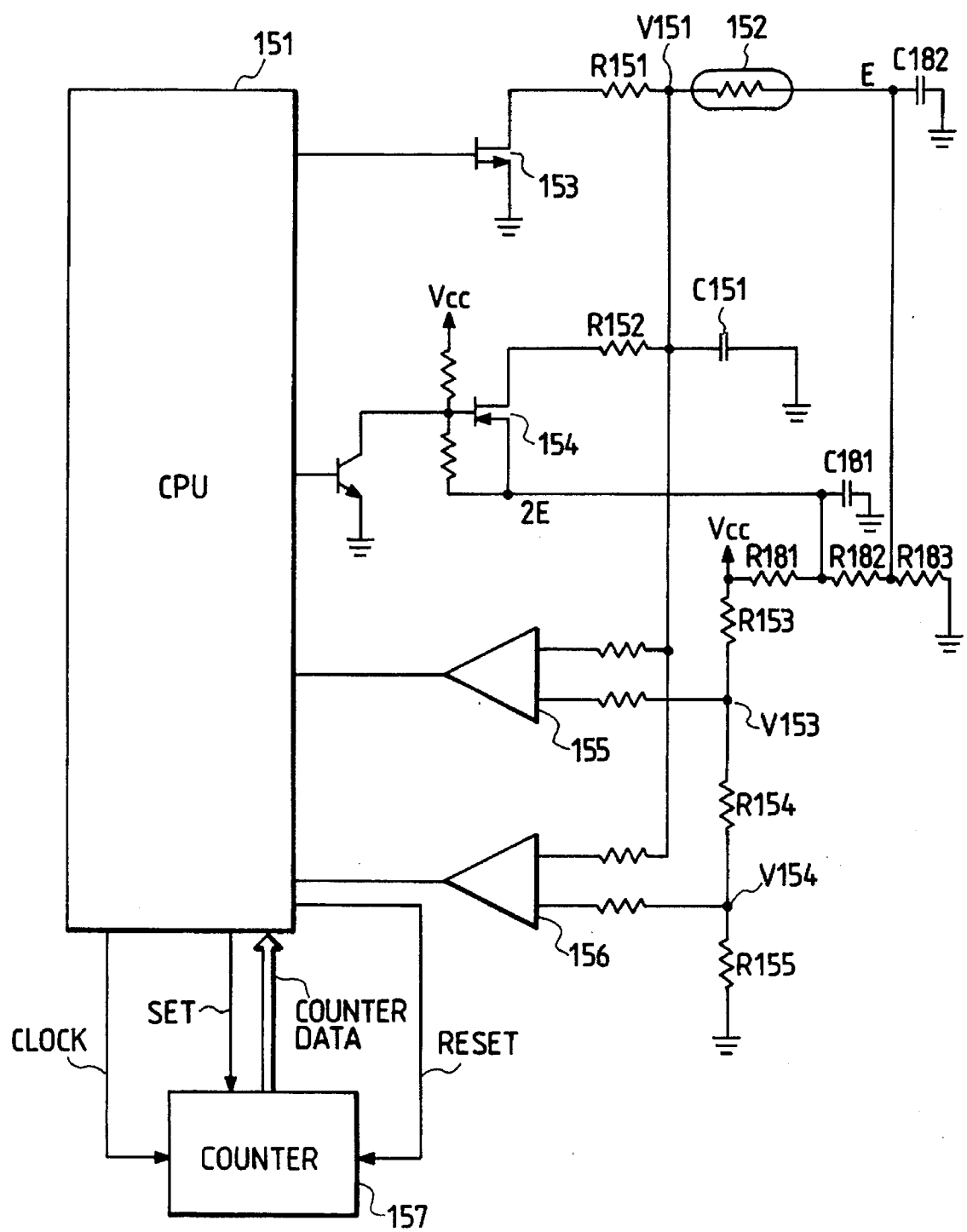
FIG. 20 is a circuit configuration diagram of a humidity measuring apparatus according to another embodiment of the present invention.

FIG. 20 is a circuit configuration diagram for providing the power voltage E, 2E in FIG. 17 from a power supply Vcc.

Figure 21:
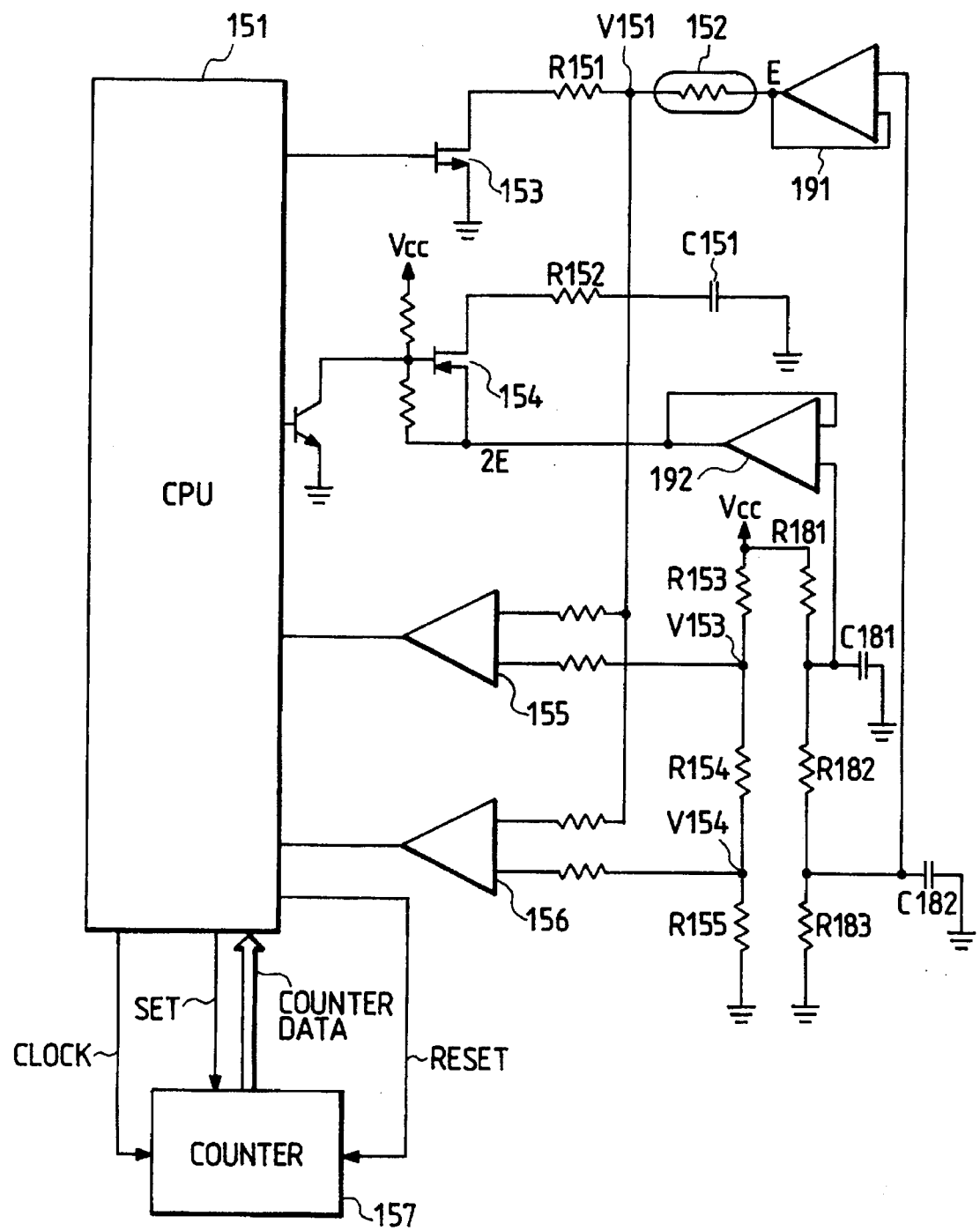
FIG. 21 is a circuit configuration diagram of a humidity measuring apparatus according to another embodiment of the present invention.

Also, FIG. 21 is a circuit configuration diagram in which the voltages E, 2E are supplied via voltage followers 191, 192 in order to raise the accuracy of reference voltage. Thereby, the measurement environment is never disturbed by the Joule heat of the resistor produced by the decrease in power efficiency when the partial pressure resistance is decreased to suppress the measurement error in the high humidity measurement.

With such a circuit configuration, the resistance RS of humidity sensor 152 is obtained, and thus the humidity is obtained as in the previous embodiment.

Figure 22:
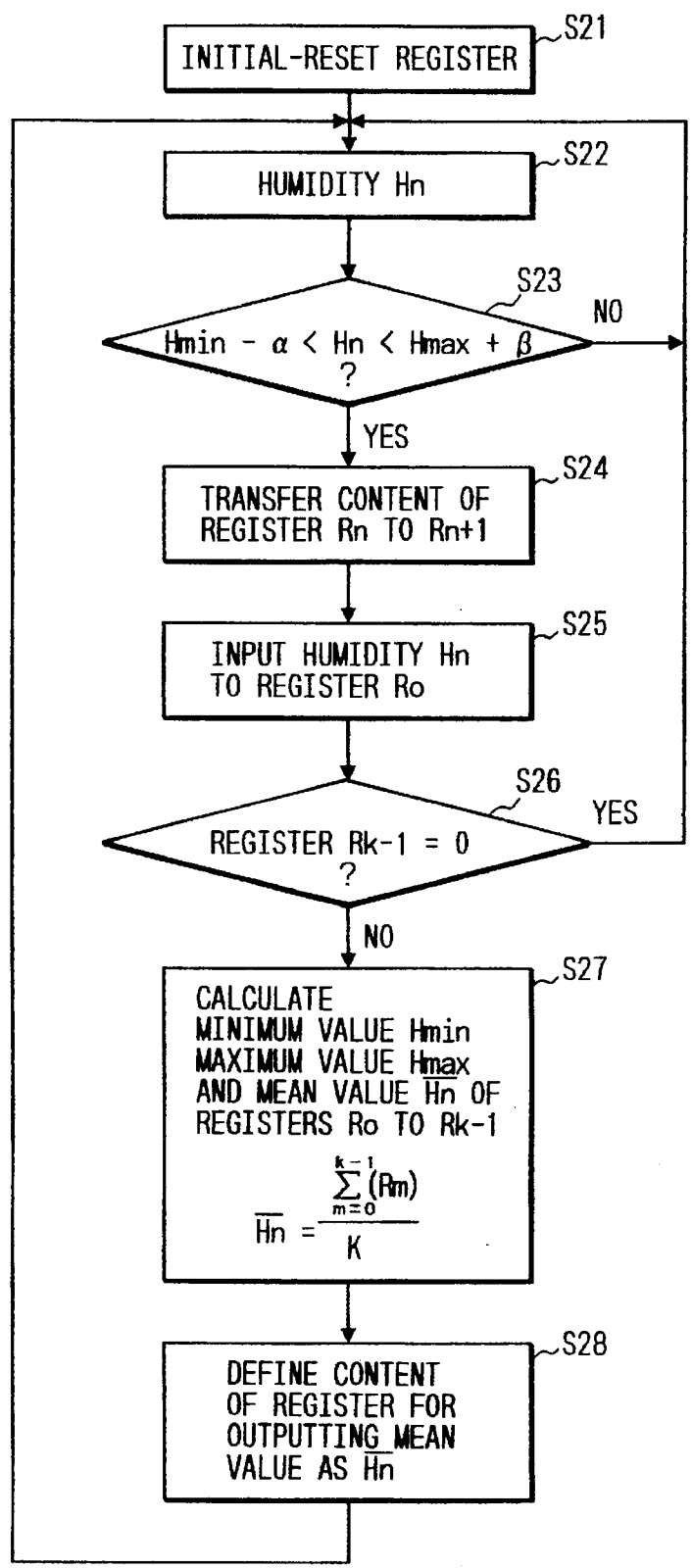
FIG. 22 is a flowchart for permitting the stable humidity measurement with any one of the humidity measuring apparatuses of FIGS. 17, 20 and 21.

FIG. 22 shows a flowchart for allowing the stabler humidity measurement by judging the humidity data obtained by the previously described method for the properness, and taking the average value (mean value) of a predetermined number of data.

First, registers of the microcomputer 151 are initialized (step S21), and the calculated humidity data Hn is input (step S22). And the comparison is made between the maximum value Hmax and the minimum value Hmin of the humidity data and the input humidity data Hn (step S23). If the humidity data Hn is greater than (Hmin-α) and smaller than (Hmax+β), the humidity data is updated (where α, β are constant). If the humidity data Hn is out of the range at step S23, the routine proceeds to step S22. When the humidity data is updated, the contents of the registers $R_0$ to $R_{K-1}$ are transferred to the registers $R_1$ to $R_K$ (step S24), and the humidity data Hn is input to the register $R_0$ (step S25).

And if the content of the register $R_{K-1}$ is still zero, the routine proceeds to step S22, or otherwise to the next step (step S26). If $R_{K-1}$ is not equal to zero at step S26, the minimum value Hmin and the maximum value Hmax among the registers $R_0$ to $R_{K-1}$ are obtained, respectively, and further the average value of the humidity data is obtained by the following expression (step S27).

$$FN = \sum_{m=0}^{K-1} (Rm)/K$$

And the content of an average value output register is defined as Hn (step S28), and the routine proceeds to step S22.

In this way, the stabler humidity measurement can be made by updating the average value.

EMBODIMENT 8

Figure 23:
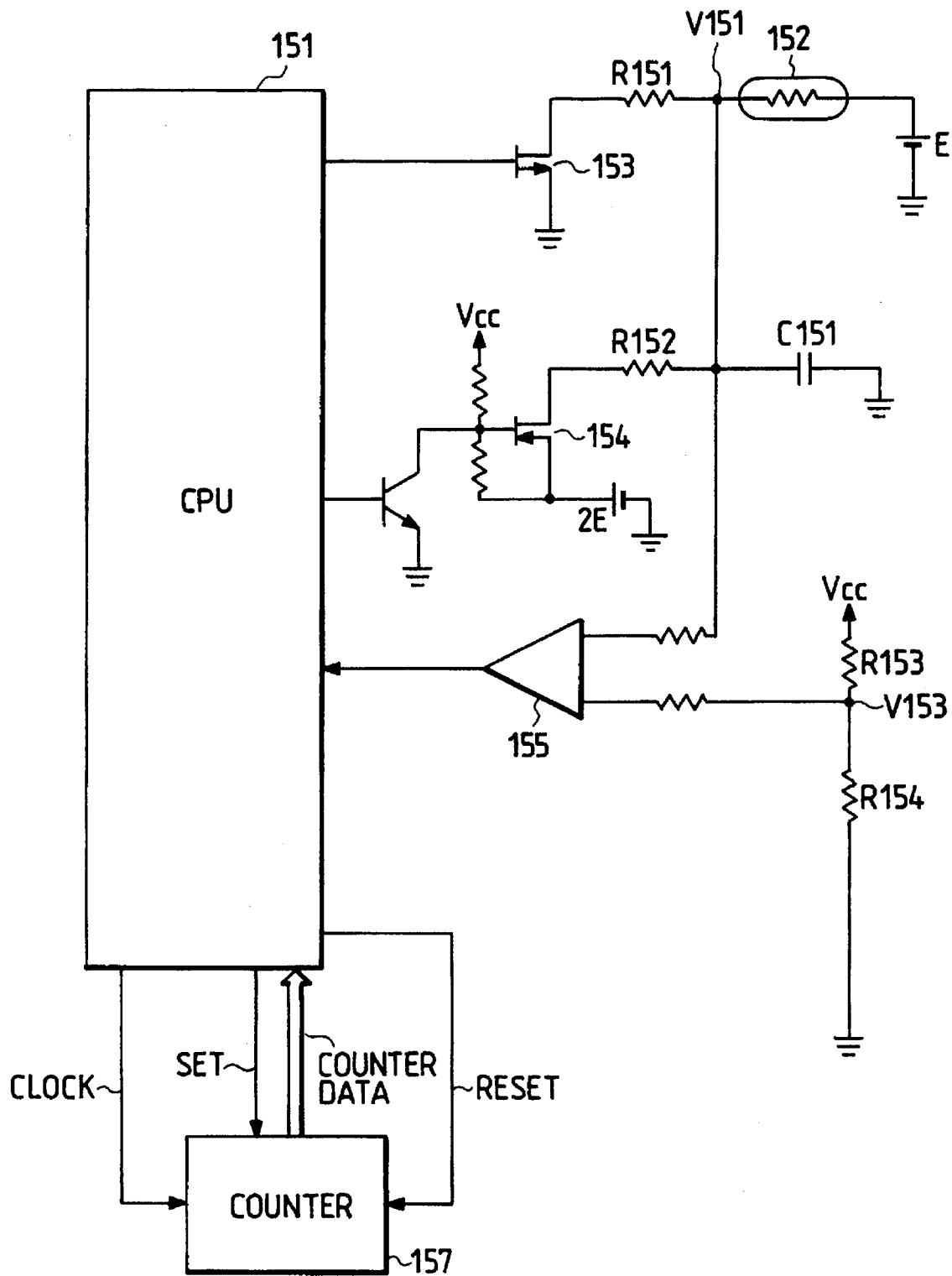
FIG. 23 is a block configuration diagram of a measuring apparatus according to another embodiment of the present invention.

FIG. 23 is a circuit configuration diagram of a humidity measuring apparatus according to an eighth embodiment of the present invention. This configuration is substantially the same as that of FIG. 17, with the exception that elements 156, R155 in FIG. 17 are not provided.

Figure 24:
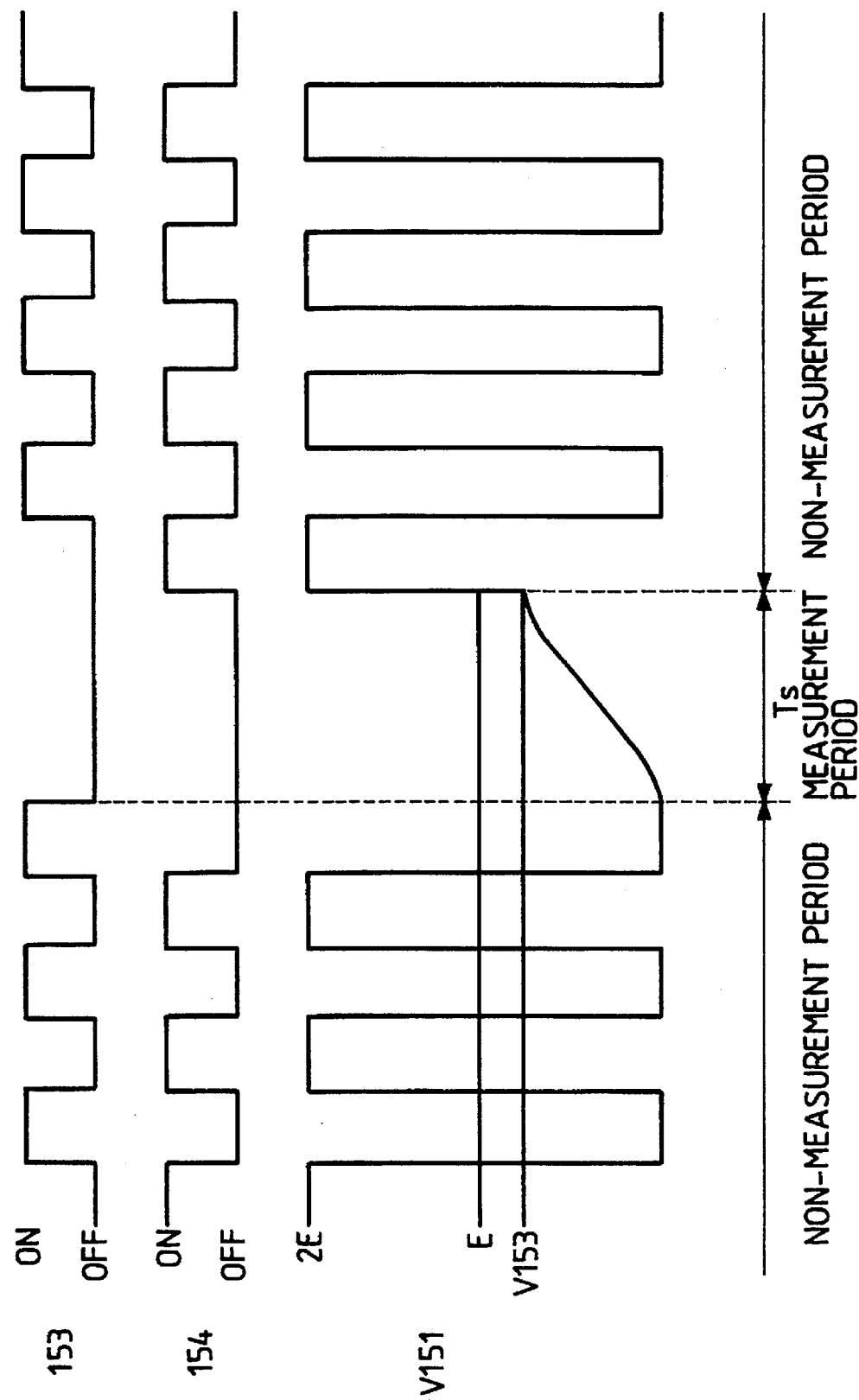
FIG. 24 is a timing chart in the measuring apparatus of FIG. 23.

FIG. 24 is a control timing chart for switches 153, 154.

As shown in FIG. 24, the control timing for the electronic switches 153, 154 when not measured is controlled by switching them so that the AC voltage having a predetermined frequency is applied across the sensor to reduce the deflection in the ion distribution inside the humidity sensor 152 which may occur in the measurement. With one end of the humidity sensor 152 fixed at a voltage E, the voltages 0[V] or 2E[V] is applied at a predetermined frequency f to the other end thereof. Depending on the kind of sensor element for use, the control is performed at a numerical example of E=about 1[V], f=about 1[kHz].

When the measurement is made, both the electronic switches 153, 154 are turned off in a state where the electronic switch 153 is on and the condenser 151 is discharged, and charging of the condenser C151 is started in a state where a voltage E is applied to a series circuit of the humidity sensor 152 and the condenser C151. In this embodiment, the detection voltage is set up at a voltage at which charging is allowed within a period of ten times or less the maximum frequency in the AC application service range to the sensor element, even if the resistor is in a condition where the sensor resistance is largest in a measurement range as the humidity measuring apparatus, i.e., typically in the lowest humidity environment, so that the deflection in the ion distribution inside can be rapidly relieved by the application of a stable AC voltage which is started immediately thereafter, thereby greatly improving the element life. For example, in the case of a high-molecular type humidity sensor generally used for the public or industrial use at present, the resistance is about 1 GΩ at a temperature of 15° C. and a humidity of about 5%, but when the condenser is 30 pF and the applied voltage is 1 V, the measurement is terminated in about 50 ms, if the detection voltage is about 0.8 V. The maximum frequency used for the AC voltage application to the sensor element is about 10 ms, and if the time for which unidirectional electric field is continuously applied in making the measurement is about 100 ms, or ten times the maximum frequency used for the AC voltage application, the deflection of internal ions or electrons, and the polarization, can be sufficiently reduced by applying a stable AC voltage to the sensor before and after the measurement, whereby the degradation of element life can be avoided and the low humidity of 20% or less is enabled.

Detecting the time TS to reach the threshold V153 after the start of charging, the sensor resistance RS can be calculated by using the following expression.

$$RS=TS/(C1 \cdot \log(1-V153/E)))$$

From the sensor resistance RS thus measured, the relative humidity can be obtained in the following way.

Figure 15:
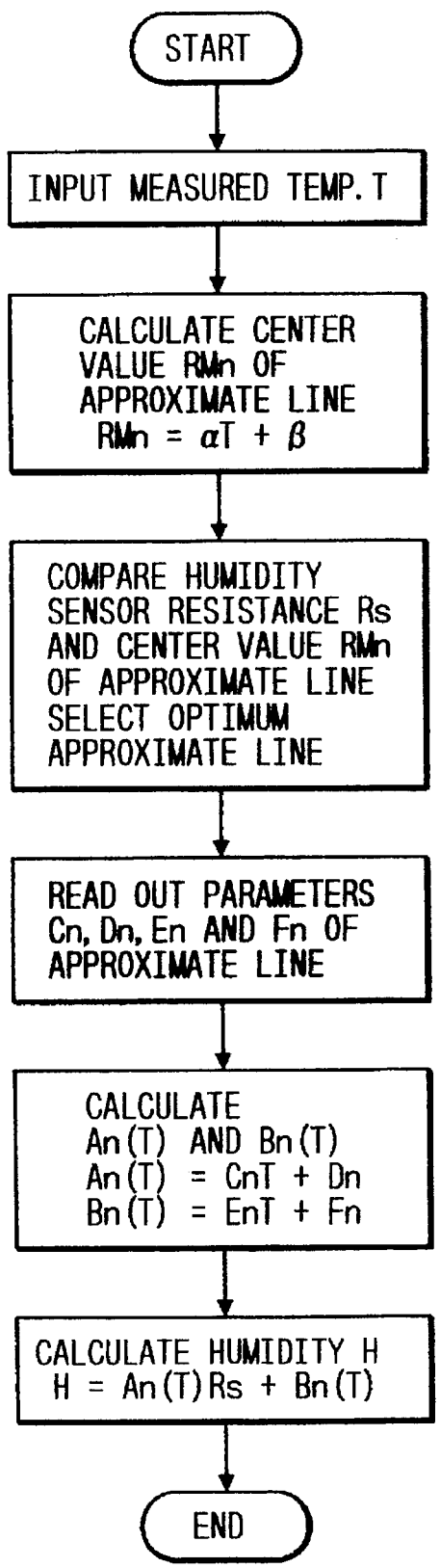
FIG. 15 is a flowchart showing the flow for measuring the humidity with the humidity measuring apparatus of FIG. 12.

The output curve of the sensor is linearly approximated by dividing it into five regions at each temperature, as shown in FIG. 14. In accordance with the flowchart as shown in FIG. 15, the flow of obtaining the relative humidity will be described.

From the sensor resistance RS and the ambient temperature T measured by a temperature sensor, not shown, provided near the humidity sensor 2, the linear approximation range is selected, and the line parameters Cn, Dn, En, Fn are obtained from a lookup table prestored in the CPU.

AN(T), BN(T) are obtained from RS, T, Cn, Dn, En and Fn. And from AN(T) and BN(T) thus obtained, the relative humidity H is obtained.

As previously described, by applying the AC voltage when not measured, the continuous application of unidirectional electric field can be relieved to about ten times the maximum frequency used for the AC voltage application, but for a longer measurement time, the element resistance is rapidly increased, and the charging speed is rapidly decreased due to the influence of parallel resistances of the condenser as well as the substrate pattern, and the leakage current, and at the worst case, the charging may not be made even to one-half or greater the applied voltage, while if the sensor resistance exceeds 1 GΩ in the low humidity environment, the measurement is not terminated within a period of the continuous application of electric field, whereby there is a danger of causing a unrecoverable damage to the sensor element. When such a danger exists, it is necessary that the threshold voltage is set at about one-fifth an applied voltage as previously mentioned, as indicated by V153' in FIG. 25.

Figure 26:
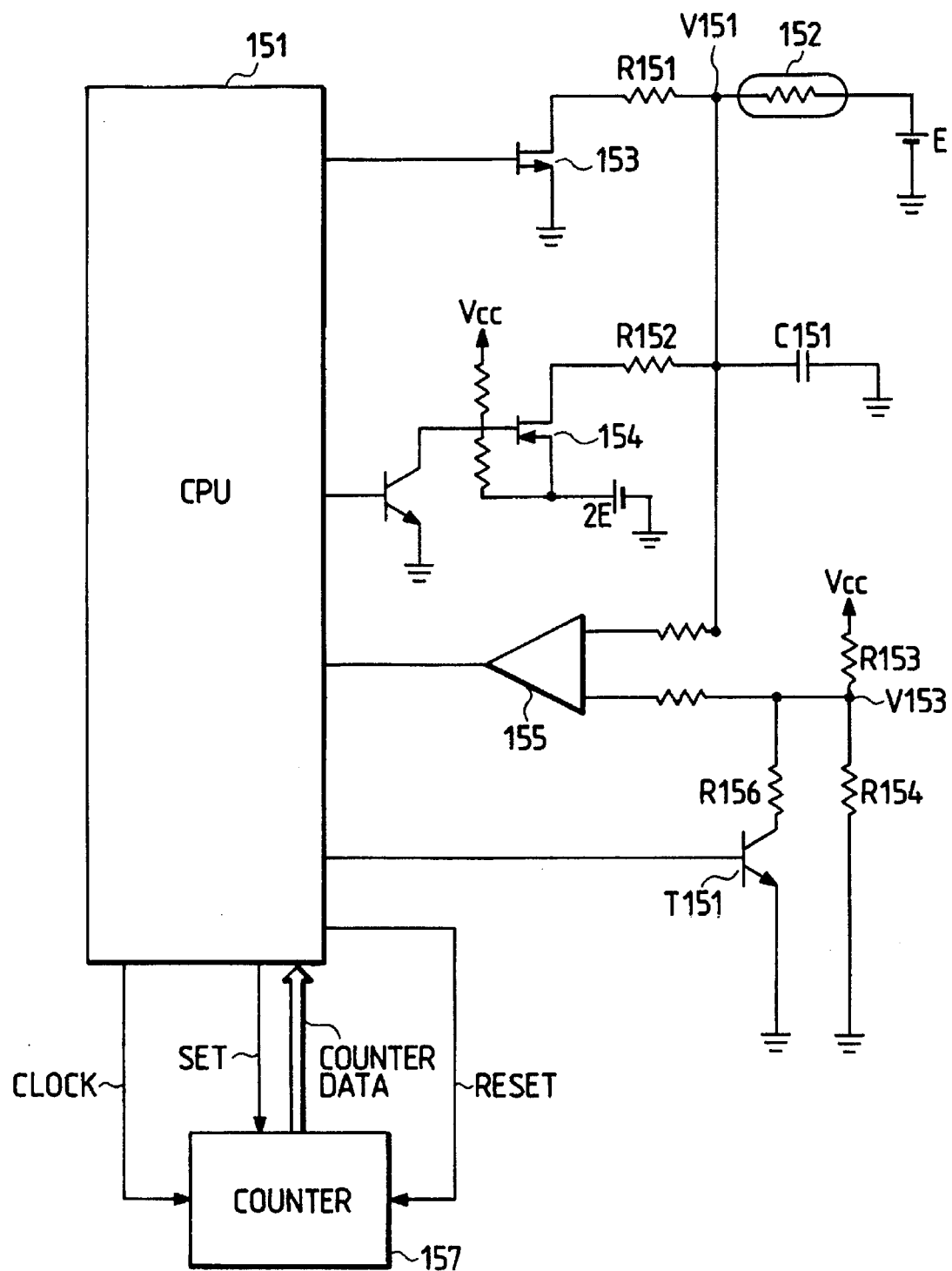
FIG. 26 is a block configuration diagram of a measuring apparatus according to another embodiment of the present invention.

As shown in FIG. 26, the measurement is allowed by controlling a transistor T151 with the output signal from the microprocessor to switch the threshold of comparator using R154 and R156.

EMBODIMENT 9

Figure 27:
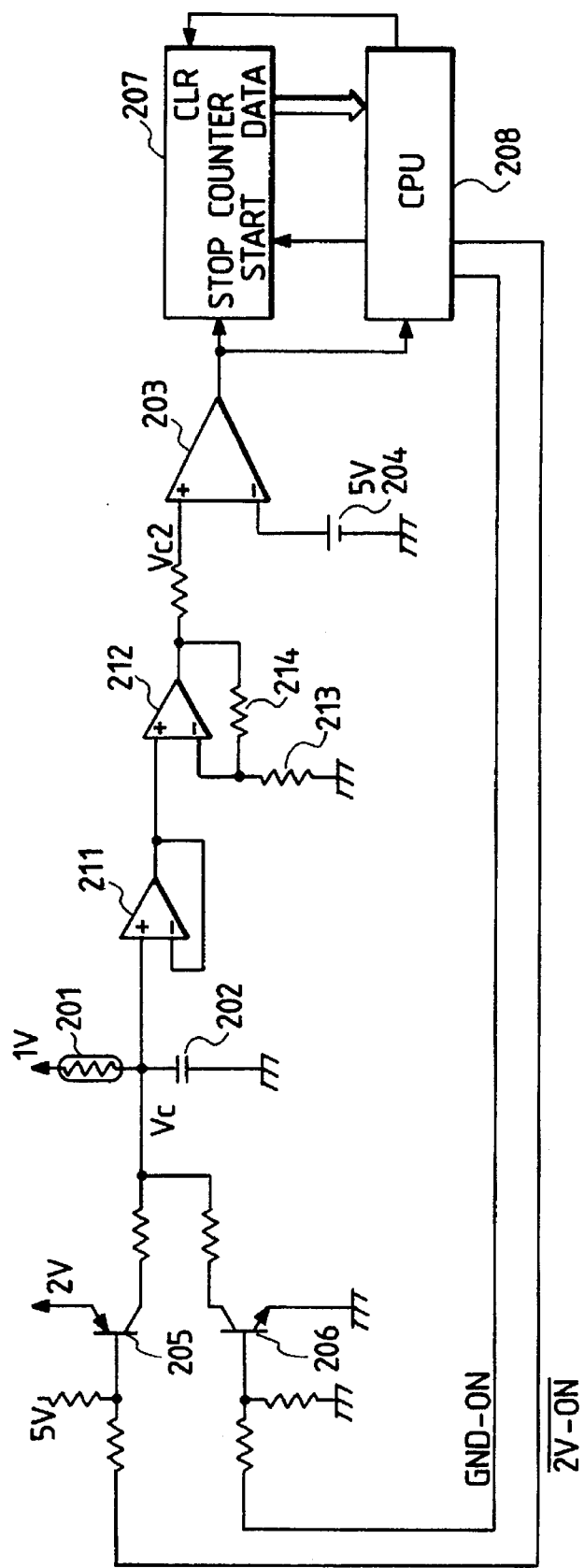
FIG. 27 is a block configuration diagram of a measuring apparatus according to another embodiment of the present invention.

FIG. 27 is a circuit configuration diagram of a humidity measuring apparatus according to a ninth embodiment of the present invention. The element 201 is a humidity sensor element having its electric conductivity varied with the relative humidity. One side of the humidity sensor 201 is connected to a constant voltage source of 1 V. The element 202 is a charging condenser, the element 203 is a comparator for comparing the voltage of charging condenser 202 with a predetermined value, the element 204 is a comparison voltage generator, the element 205 is a switch element for applying a voltage of 2 V to the humidity sensor 201 on the opposite side to which 1 V is applied at a predetermined timing, the element 206 is also a switch element for applying 0 V, the element 207 is a counter circuit for measuring the charging time, and the element 208 is a controller for controlling the system, consisting of a board mounted with a so-called one-chip microcomputer. The element 211 is an impedance converter consisting of an operational amplifier, which converts the charging voltage of charging condenser 202 to the low impedance to transmit it to the next stage. The element 212 is an amplification circuit consisting of an operational amplifier as well, with its degree of amplification determined by resistors 214, 213.

Figure 28:
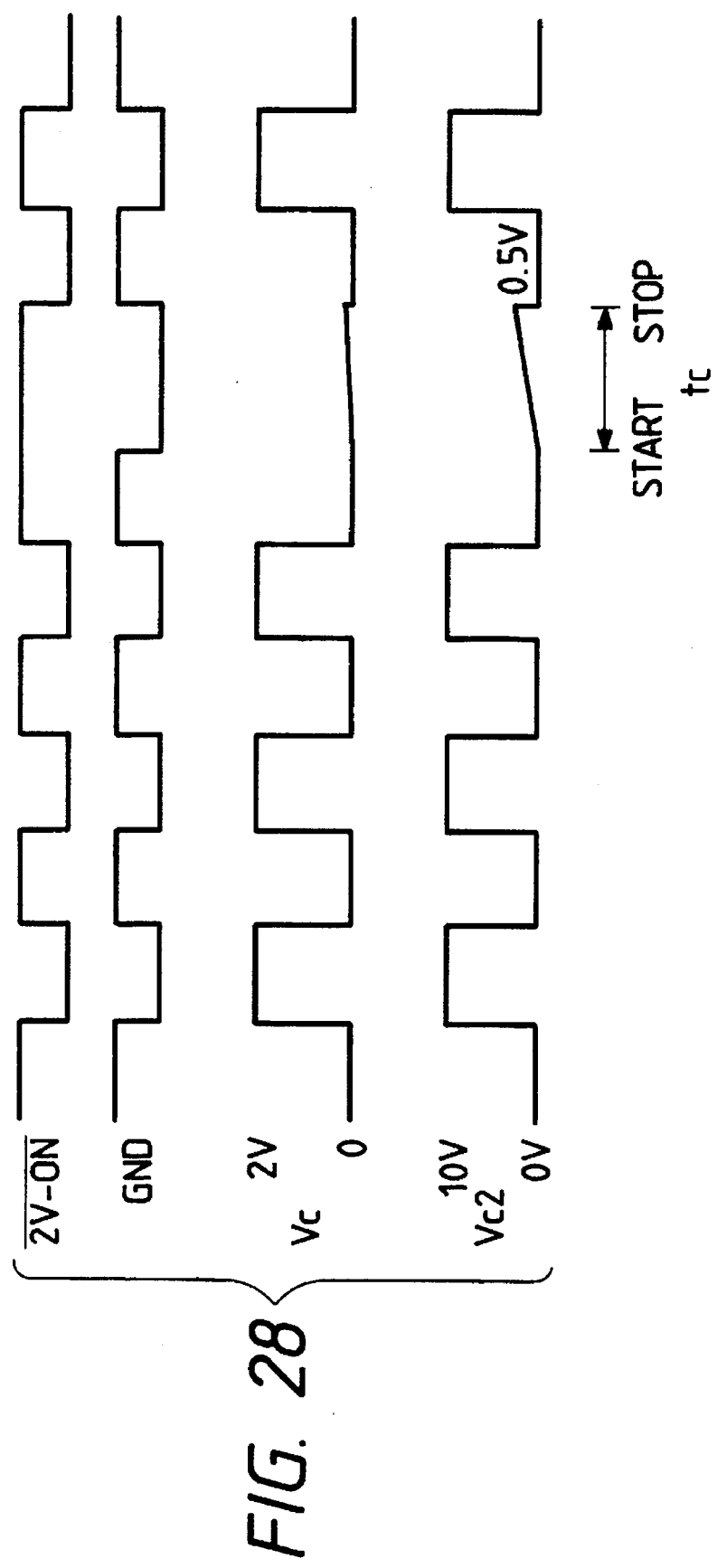
FIG. 28 is a timing chart in the measuring apparatus of FIG. 27.

With the above configuration, the operation will be described. When not measuring, the controller 208 alternately turns on switch elements 205, 206 at a frequency of about 1 KHz (see FIG. 28). By doing this, 2 V and 0 V are alternately applied to the opposite side of sensor 201 to which a voltage of 1 V is applied, so that the AC voltage of ±1 V is applied across the sensor 201.

When measuring, the controller 208 disables the switch element 205 at the timing when the switch element 205 is turned on, and at the same time makes a clear signal to the counter circuit 207 invalid and a start signal valid. Thereby, a series circuit of charging condenser 202 and humidity sensor 201 enters the charging operation with a power supply of 1 V, and the counter circuit 207 starts the count operation with a clock provided inside.

The charged voltage is amplified at a predetermined amplification factor by the impedance converter 211 and the amplifier 212, and detected to reach a predetermined voltage by the comparator 203.

When the amplified voltage exceeds a predetermined voltage, the output of the comparator 203 gets high, and a stop signal is issued to the counter 207. Upon detecting this stop signal, the controller 208 reads the counter value or the time for reaching a predetermined charging voltage. Thereafter, based on this value, the resistance of the humidity sensor 201 is obtained, and the relative humidity is determined based on this resistance and a temperature value measured by another block.

With this configuration, even if the humidity sensor 201 has a high resistance of about several tens GΩ to lower the charging speed, the time to reach a predetermined value can be shortened because of the expanded charging state for the detection, whereby the degradation of element caused by the continuous application of a unidirectional voltage to the sensor element can be avoided. Note that the influence of amplification must be taken into consideration in calculating the sensor resistance for a measured charging time.

In the previous embodiment, when the sensor element has several tens GΩ in a low humidity condition, it is necessary to set up the amplification factor so that the measurement may be terminated within a predetermined period. Accordingly, when the resistance of the sensor element at high humidity is lowered to several tens kΩ, the time to reach a predetermined charging voltage is shortened by more than several digits, and a counter circuit using a high speed original clock is needed to measure that time accurately.

EMBODIMENT 10

Figure 29:
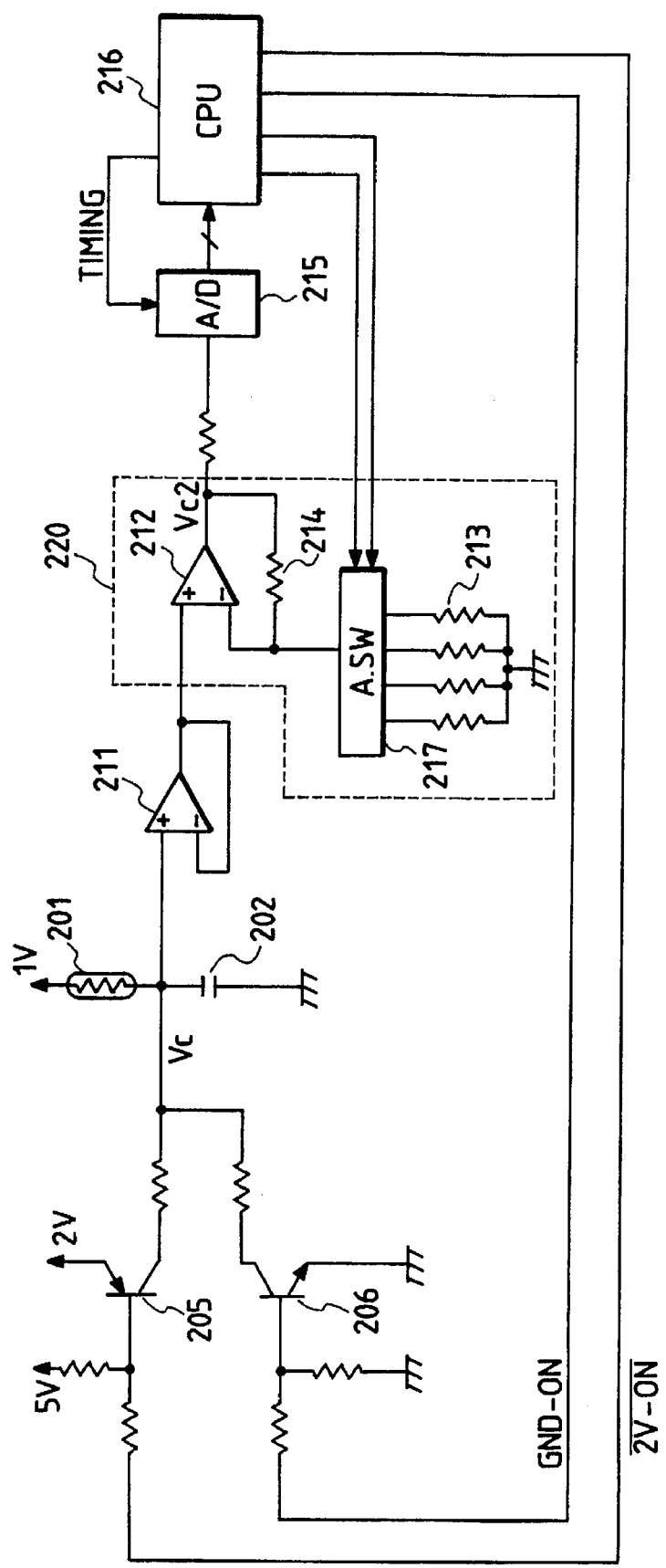
FIG. 29 is a block configuration diagram of a measuring apparatus according to another embodiment of the present invention.
Figure 30:
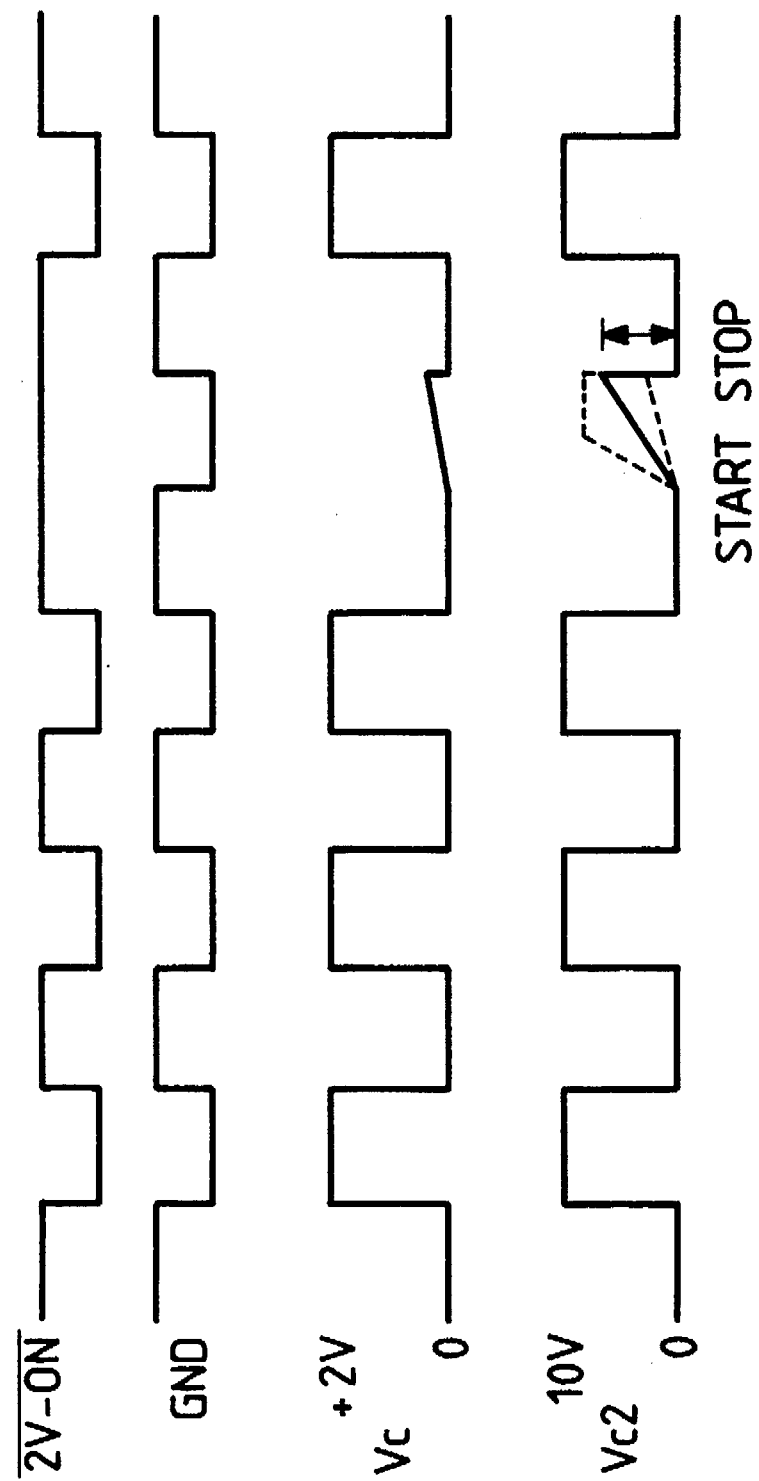
FIG. 30 is a timing chart in the measuring apparatus of FIG. 29.
Figure 31:
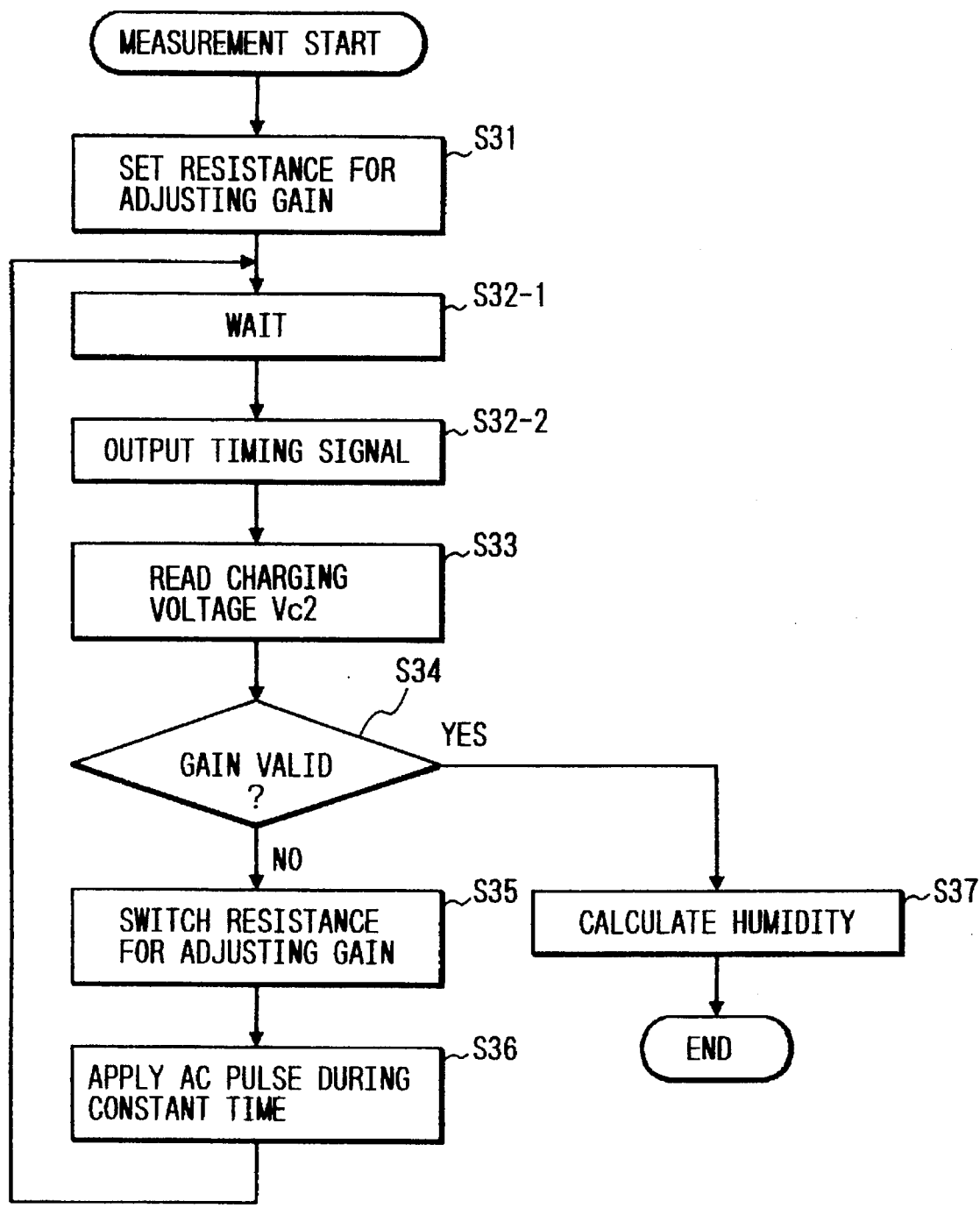
FIG. 31 is a flowchart for calculating the humidity.

Referring now to FIGS. 29, 30 and 31, the tenth embodiment will be described. The feature of this embodiment resides in appropriately switching the amplification factor of amplification circuit so that the charging voltage may fall within a predetermined range in a predetermined time.

In FIG. 29, a block 220 is an amplification circuit having the amplification factor switchable by a control signal from a CPU 216. An operation procedure will be described with reference to a timing chart of FIG. 30 and a flowchart of FIG. 31. First, when not measured, the pulse wave of ±1V is stably applied across the humidity sensor 201. And when measured, the 2 V side and the ground side are separated from the circuit. The CPU 216 outputs the same control signal as at the previous measurement, with the same amplification factor set as previously (step S31). And after a predetermined time (for which no element degradation is caused by the continuous application of unidirectional electric field), the CPU 216 outputs a timing signal to an A/D conversion circuit 215 (step S32), and performs the sample-and-hold and the A/D conversion for amplified charging voltage of a condenser to read a charging voltage value (step S33). When this value is within a predetermined range (step S34), the CPU 216 calculates the resistance of the humidity sensor 201, in consideration of the amplification factor and the charging time, from the amplified value of the charging voltage at this time, and calculates the humidity based on the resistance (step S37). On the other hand, when the amplified value of the charging voltage is not within a predetermined range (step S34), for example, when the charging voltage is low the control value from the CPU 216 is switched (step S35), the measurement is retried with a raised degree of amplification. Note that to supply a stable AC electric field to the humidity sensor 201, the application of AC pulse is performed for a suitable period before starting the measurement, when the measurement is retried (step S36). Thereby, the resistance of humidity sensor 201 can be measured without demanding high precision to A/D converter or each component, whereby a humidity measuring apparatus for the measurement in a wide range from low to high humidity can be provided inexpensively.

While in the previous embodiment the sensor resistance was obtained by switching the amplification factor appropriately to amplify the voltage to be charged within a certain period to a value in a certain range, it will be appreciated that the measurement may be performed by setting the charging time as short as possible to relieve the load on the humidity sensor 201, and optimizing (making shortest) the charging time.

Figure 32:
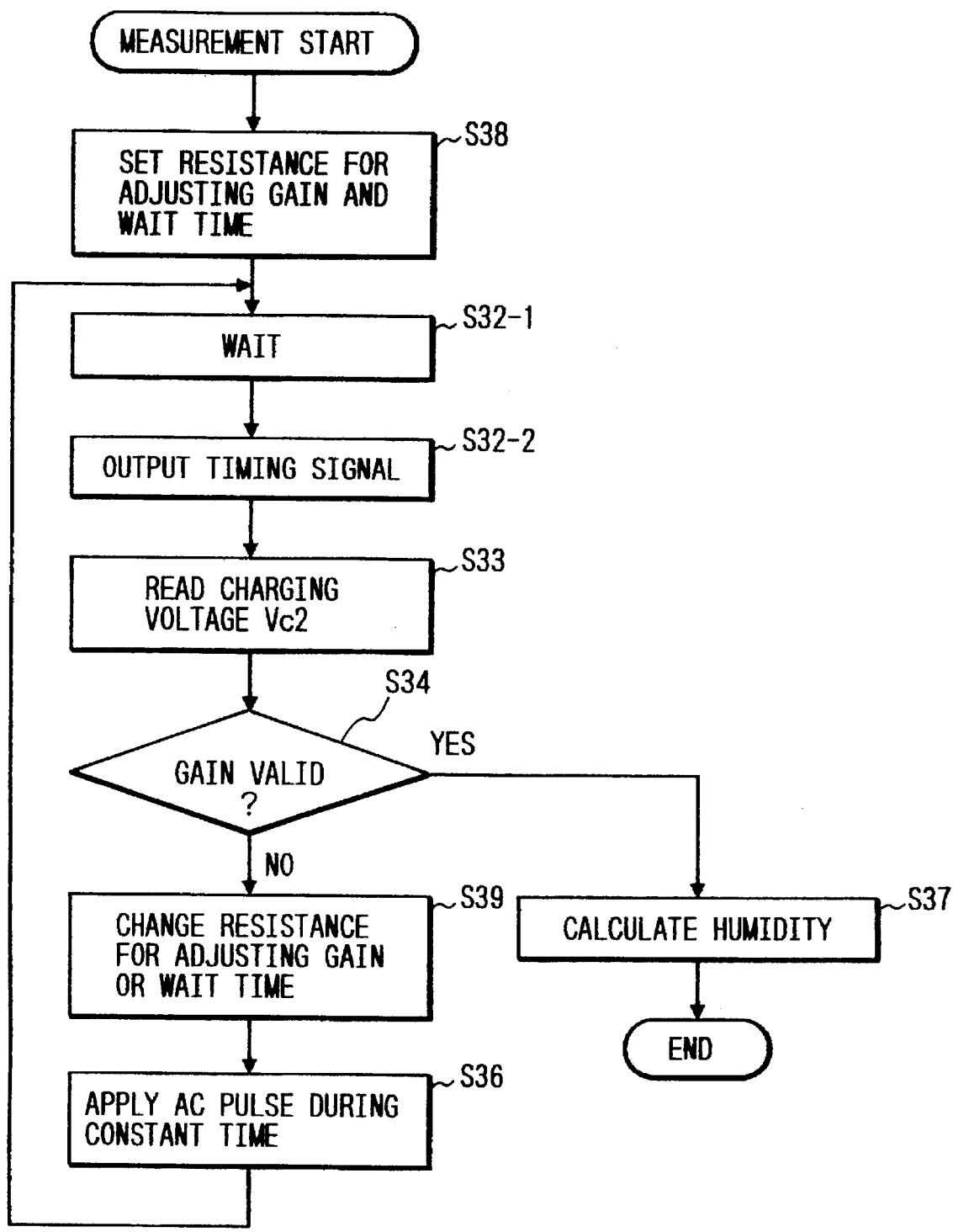
FIG. 32 is a flowchart for calculating the humidity.

As shown in a flowchart of FIG. 32, first, the charging time is set at the least value (e.g., 10 µS) (step S38), and the optimization of amplification degree is performed in the same procedure as in FIG. 31. If a predetermined voltage is not reached even at the maximum amplification degree due to a high sensor resistance, the charging time is set to be longer (e.g., 10 ms) (step S38), and the optimization of the amplification degree is performed in the same procedure.

In this way, since the charging time can be observed by extending it in time and voltage, the application time of unidirectional electric field applied to the sensor element is restrained to no more than a predetermined value, and a humidity measuring apparatus can be realized in which the high resistance such as several tens GΩ can be measured in a short time, and the low humidity region of 5 to 20% can be measured.

EMBODIMENT 11

Figure 33:
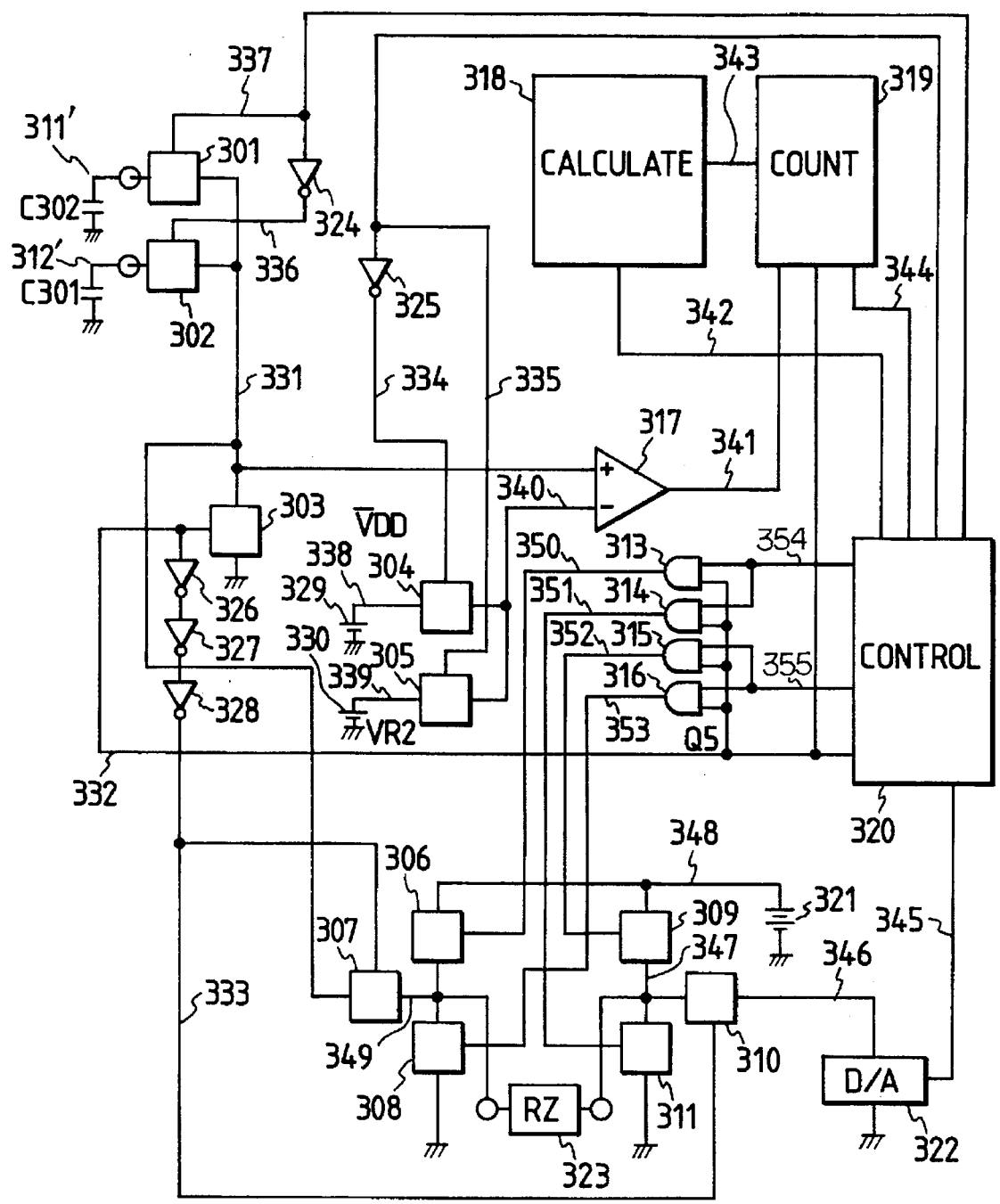
FIG. 33 is a block configuration diagram of a measuring apparatus according to another embodiment of the present invention.

FIG. 33 is a circuit configuration diagram of a humidity measuring apparatus according to an eleventh embodiment of the present invention. Elements 301 to 311 are analog switches, for use in applying a rectangular wave signal to a humidity sensor 323, connecting the humidity sensor 323 to a D/A converter 322, connecting the humidity sensor 323 to condensers C301, C302, or connecting comparison reference power sources 329, 330 to a minus input terminal of a comparator 317.

Elements 313 to 316 are two-input AND gates for controlling the switching timing of analog switches 306, 308, 309 and 311. Elements 321, 329, 330 are reference power sources each having a fixed voltage. Element 322 is a D/A converter for the variable power supply for use in measuring the resistance of the humidity sensor, wherein a control signal is fed via a signal line 345 by a control portion 320 to switch the digital data. A result counted by a count portion 319 can be calculated by an operation portion 318 to obtain the humidity. Elements 324 to 328 are inverter circuits which are elements for outputting the inverted input signal. The above components are connected as follows.

The other ends of the condensers C301, C302 with one ends grounded are connected to one ends of the analog switches 301, 302, respectively, and the other ends of the analog switches 301, 302 are connected via a signal line 331 to a + signal input terminal of the comparator 317, a signal input terminal of the analog switch 303 with the other end grounded, and one signal input terminal of the analog switch 307. One signal input terminals of the analog switches 304, 305 are connected via signal lines 338, 339 to + terminals of reference power sources 329, 330, respectively. Also, the other signal input terminals of the analog switches 304, 305 are connected to one signal input terminal of the comparator 317 via a signal line 340.

The other signal input terminals of the analog switch 308 with one signal input terminal grounded are connected via a signal line 349 to one signal input terminals of the analog switches 307, 306 and one terminal of the humidity sensor 323, and likewise, the other signal input terminals of the analog switch 311 with one signal input terminal grounded are connected via a signal line 347 to one signal input terminals of the analog switches 309, 310 and the other terminal of the humidity sensor 323. The other signal input terminals of the analog switches 306, 309 are both connected via a signal line 348 to the + terminal of a power source 321 with the minus terminal grounded, and the other signal input terminal of the analog switch 310 is connected via a signal line 346 to an analog signal output terminal of a D/A converter 322. A control terminal of the analog switch 301 is connected via a signal line 337 to a control signal output terminal of a control unit 320. The input of an inverter 324 is connected via the signal line 337 with the output thereof connected via the signal line 336. And the signal line 336 is connected to a control terminal of the analog switch 302. Likewise, the control terminal of analog switch 305 is connected via the signal line 335 to a control signal output terminal of the control unit 320. The input of the inverter 325 is connected via the signal line 335 with the output thereof connected to the signal line 334. And the signal line 334 is connected to the control terminal of the analog switch 304. The control terminals of the analog switches 307, 310 are connected via the signal line 333 to the output terminal of the inverter 328.

The control terminals of the analog switches 306, 308, 309, 311 are connected via signal lines 350, 351, 352, 353 to the output terminals of two-input AND gates 313, 314, 315, 316, respectively, with one input terminals of the AND gates 313, 314, 315, 316 connected via the signal line 332 to a control signal output terminal of the control unit 320. The other signal input terminals of the AND gates 313, 314 are connected via the signal line 354 to the control signal output terminal of the control unit 320. The signal line 332 is also connected to a control terminal of the analog switch 303 and an input terminal of inverter 326. Elements 326, 327, 328 are inverters, three inverters constituting one delay element, with the signal output terminal of the inverter 326 being connected to the signal input terminal of the inverter 327, and the signal output terminal of the inverter 327 being connected to the signal input terminal of the inverter 328. The signal output terminal of the comparator 317 is connected via the signal line 341 to the signal input terminal of count unit 319. Also, the digital signal input terminal of D/A converter 322 is connected to the digital control signal output terminal of the control unit 320. The control unit 320 and the count unit 319 are interconnected via a bidirectional signal line 344.

Also, the count unit 319 outputs the operation information via the signal line 343 to the operation unit 318. The operation unit 318 is connected via the signal line 342 to the control signal output terminal of the control unit 320. Also, the signal line 332 is connected to the control signal input terminal of the count unit 319.

Figure 36:
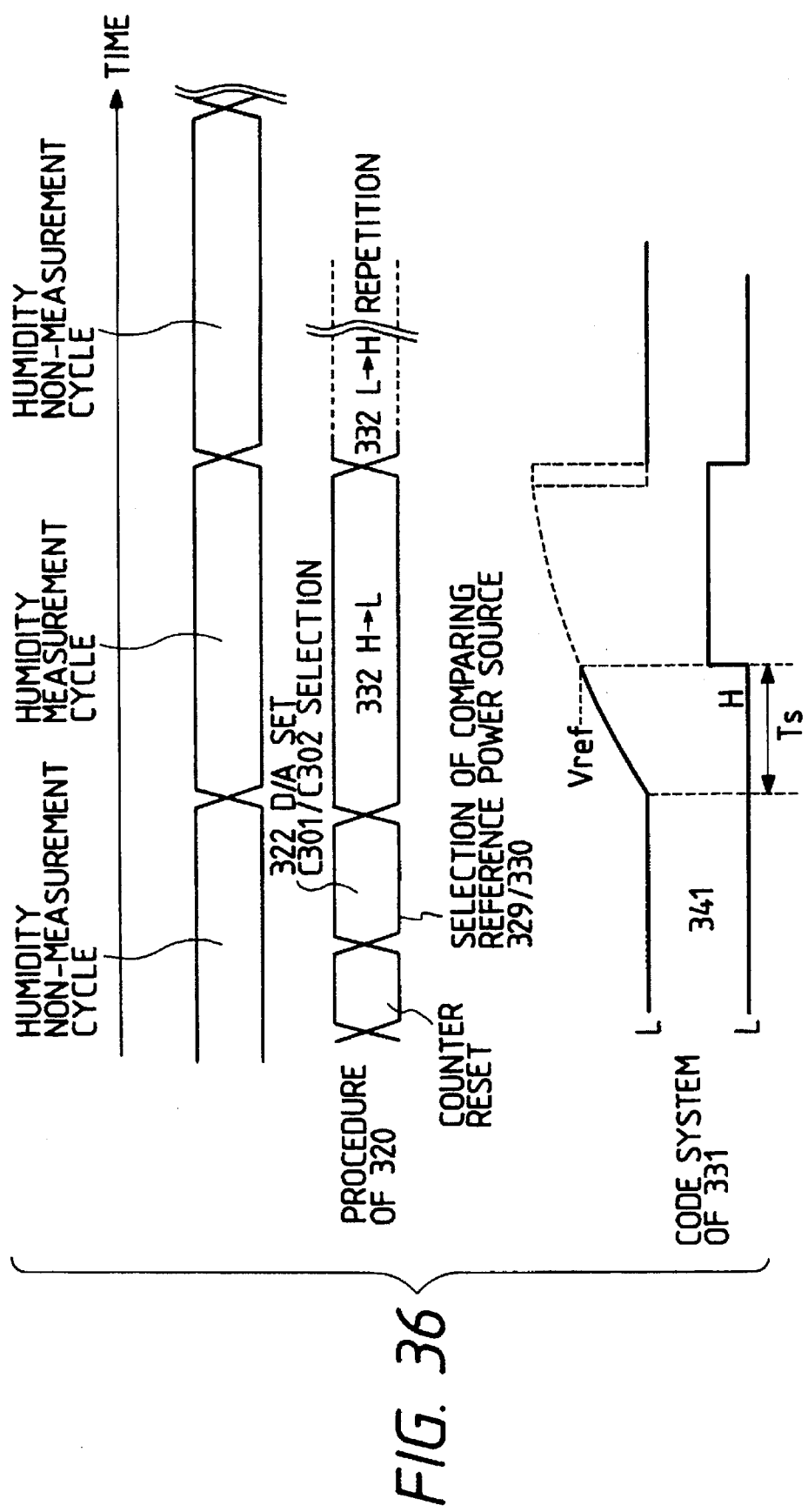
FIG. 36 is a timing chart in the measuring apparatus of FIG. 33.

Next, the operation will be described. FIG. 36 is an operation timing chart.

Figure 25:
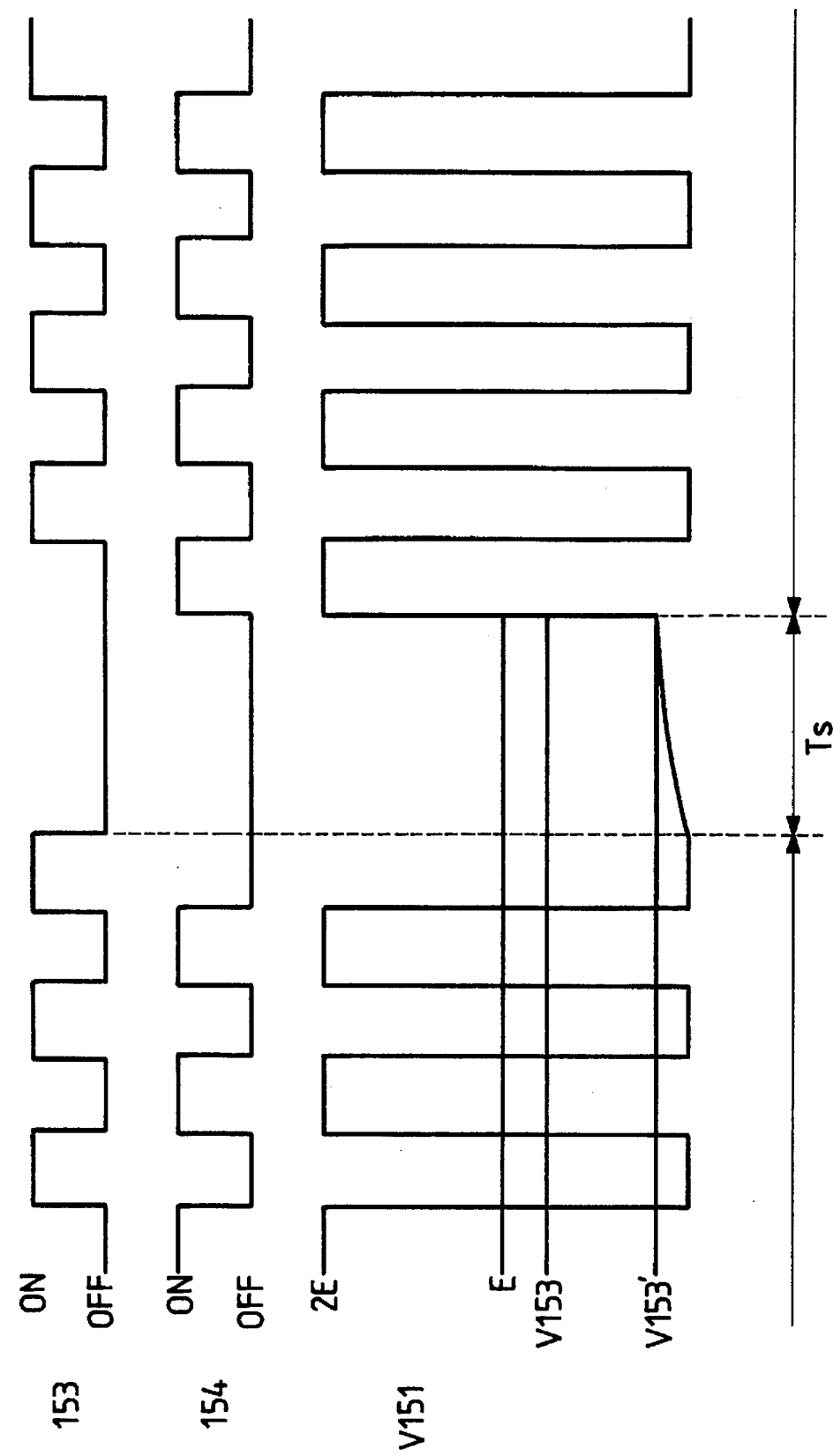
FIG. 25 is a timing chart in the measuring apparatus of FIG. 23.

When the humidity measurement is not made, the control unit 320 outputs a rectangular wave of reverse phase having a duty of 50% to the signal output terminals of 354, 355, while at the same time outputting a signal H via the signal line 332 to make the AND gates 313 to 316 active and turn on the analog switch 303 to fix the potential of the signal line 331 at a ground level. In this state, when H is output to 354 and L to 355, the analog switches 306, 311 are turned on, and the analog switches 309, 308 are turned off. Likewise, when L is output to 354 and H is output to 355, the analog switches 306, 311 are turned off, and the analog switches 309, 308 are turned on. And the signal line 333 becomes L, with the analog switches 307, 310 being off. In this state, the rectangular wave of a duty 50% having an amplitude twice that of a voltage from the power source 321 is applied to the humidity sensor 323, as shown in FIG. 25. Usually, this frequency is within a range of about 50 Hz to 100 kHz. Next, the humidity measurement procedure will be described. The control unit 320 sets the normal set voltage digital data to the digital input terminal of D/A converter 322 in a state where the humidity measurement is not made. At the same time, H is output to the signal line 337, with the analog switch 301 turned on, and the analog switch 302 turned off, and an optimal capacity of the condenser C302 to measure the medium humidity region is connected to the signal line 331. Then, the condenser C302 is preset at a capacity of about 4700 PF to meet its purpose. Also, the condenser C301 is set at a capacity suitable for the low humidity measurement, e.g., about 47 PF.

At the same time, H is output to the signal line 335, with the analog switch 305 turned on, and the analog switch 304 turned off, and an optimal comparison reference power source 330 to measure the medium resistance region is connected to the signal line 340. Then, the reference power source 330 is set at a voltage of about 0.1 V to meet its purpose. This value is sufficient to ignore the influence of the floating capacity dependent upon the voltage as with an analog switch to offer a good precision. The power source 329 is set at a voltage of about 0.3 V to provide a noise margin, when the noise causes the problem.

The measurement procedure under these conditions will be described below. The control unit 320 outputs L to a measurement time signal line 332. As a result, all the AND gates 313 to 316 are turned off, with their outputs being L. And all the analog switches 306, 308, 309, 311 are turned off. At the same time, the analog switch 303 is turned off, with the signal line 331 being in a floating state.

At the next timing, the signal line 333 becomes H via the inverters 326 to 328, and the analog switches 307, 310 are turned on, so that the analog voltage output of the D/A converter 322 starts charging of the condenser C302 through the humidity sensor 323.

The control unit 320 adds H to the signal line 344 immediately before outputting L to the signal line 332, and resets the count unit 319 beforehand.

At the moment when the signal line 332 becomes L, the count unit 319 detects an L level on the signal line 332, and starts the count (the count unit 319 naturally contains a time base).

If the voltage of the signal line 331 reaches a set voltage of 0.1 V for the power source 330, the output of the comparator 317 is reversed from L to H, and upon detecting a reversed timing, the count unit 319 stops the count, and outputs its count value to the signal line 343. The operation unit 318 reads the capacity of a charging condenser in use, a set voltage for the comparison reference power source, a set analog output voltage value of the D/A converter 322, and a premeasured measurement environmental temperature via the signal line 342 into the control unit 320, which performs operations on the data of the signal line 343, based on the above conditions to obtain the relative humidity and the absolute humidity. At the same time when the signal line 341 becomes H, the control unit 320 makes the signal line 332 H, and performs the humidity non-measurement operation again.

When the count value on the count unit 319 does not reach a certain level, the control unit 320 receives its information via the signal line 344 from the count unit 319, and once returning to the humidity non-measurement operation, then it carries out the humidity measurement again after waiting for a relaxation time of 10 sec or more.

In doing so, L is set to the signal line 337, with the condenser C301 connected to the signal line 331, and the above-described humidity measurement is repeated. Also, the measurement is performed several times under the same temperature condition, and its data are averaged by the operation unit 318. In doing so, a method is taken in which during the measurement, the control unit once returns to the humidity non-measurement operation, and performs the measurement again after waiting for a relaxation time of 10 sec or more.

In this case, when the dispersion in the data exceeds a certain value, the signal line 320 adds L to the signal line 335 to switch to the power source 329 of 0.3 V, and then the measurement is performed again.

When the count value on the count unit 319 reaches a certain value, the control unit 320 receives its information via the signal line 344 from the count unit 319, and once returning to the humidity non-measurement operation, it performs the measurement again after waiting for a relaxation time of 10 sec.

In doing so, it changes the digital information on the signal line 345 to raise the analog output value of the D/A converter 322, and controls the charging time to be shortened, thereby repeating the above humidity measurement.

Note that by using analog switch for the switch in the circuit, the bidirectional signal control is enabled on one-chip IC, and the above control can be realized.

Note that the resistance of the humidity sensor is, $R = TS/(C \cdot \log(1/(1 - Vref/VAD)))$ Where R: resistance of humidity sensor C: electrostatic capacity at 311' or 312'

Vref: set voltage of comparison reference voltage source 329 or 330

VAD: analog output voltage of D/A converter 322

TS: charging time to reach Vref from 0 V of C

The operation unit 318 can readily obtain the relative humidity by making the calculation as shown in the previous embodiment.

It should be noted that since in this embodiment Vref and VAD are variable, the measurement is allowed, without discharging charges of the capacity at the start of charging, by varying Vref and VAD.

EMBODIMENT 12

Figure 34:
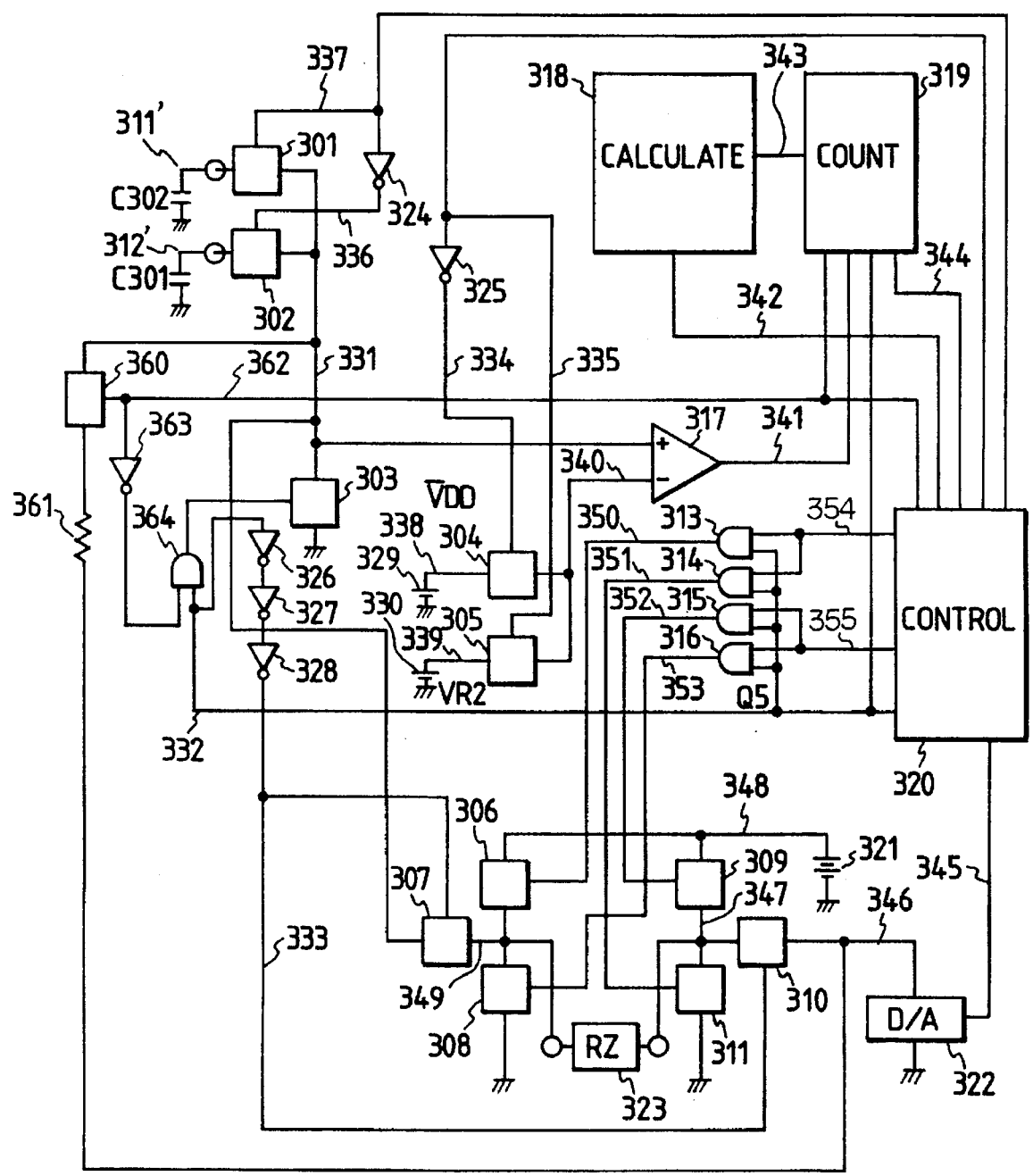
FIG. 34 is a block configuration diagram of a measuring apparatus according to another embodiment of the present invention.

FIG. 34 shows a circuit configuration diagram according to a twelfth embodiment of the present invention. FIG. 34 is one in which circuits 360 to 364 are added to the circuit of FIG. 33. Element 360 is an analog switch, with its control terminal connected to a signal line 362 leading to a control terminal of a control unit 320, with one signal input terminal thereof connected to a signal line 331, and the other signal input terminal connected to one terminal of a reference resistor 361, and the other signal terminal of the reference resistor is connected to a signal line 346. Also, the signal line 362 is connected to an input terminal of an inverter 363, with its output terminal connected to one signal input terminal of two-input AND gate 364. The AND gate 364 has been inserted as a gate circuit into a signal line 332 in the first embodiment. Specifically, in the first embodiment, the signal line 332 is separated from the control terminal of an analog switch 303, the signal line 332 is connected to the other input gate terminal of the AND gate 364, and the output terminal of the AND gate 364 is connected to the control terminal of the analog switch 303.

Next, the operation will be described. The basic operation is the same as in FIG. 33, because L is normally output to the signal line 362. It is assumed that the initial settings for the humidity measurement have been completed actually.

In a low humidity state, the sensor resistance becomes high (as large as about 1 GΩ), causing the necessity of reducing the capacity of condensers C301, C302 because of being affected by the input/output capacity of analog switch, the input capacity of comparator, and the floating capacity. Then, a reference resistor 361 is used to measure the correct capacity. That is, in the operation state at the humidity non-measurement time, the control unit 320 outputs H to the signal line 362, turning on the analog switch 360, and off the analog switch 303. As the analog switches 207, 310 are off in this state, the analog signal output voltage of the D/A converter 322 starts the charge the condensers C301, C302 through the reference resistor 361 and the analog switch 360. The control unit 320 adds H to the signal line 344 immediately before outputting H to the signal line 362, and resets the count unit 319 beforehand.

And at the moment when the signal line 362 becomes H, the count unit 319 detects an L level on the signal line 362, and starts the count (the count means 319 naturally contains a time base).

When the voltage of the signal line 331 reaches a set voltage of power sources 329, 330, the output of the comparator 317 is reversed from L to H, and upon detecting its reversal timing, the count unit 319 stops the count and outputs its count value to the signal line 343. The operation unit 318 reads the capacity of a used charging condenser, a set voltage of comparison reference power source, a set analog output voltage value of D/A converter 322, a reference resistance of the resistor 361, and a premeasured measurement environmental temperature via the signal line 342 from the control unit 320, and performs operations on the measurement time data on the signal line 343 to calculate an effective capacity on the signal line 331.

Thereafter, the control unit 320 sets the signal line 362 at L, and transfers to a normal measurement routine. And the capacity value read by the above operation unit means is used as reference capacity data for the humidity calculation in subsequent measurement. This operation may change depending on the environmental change, and at the worst case, the above capacity calculation processing should be always performed before the measurement, and further, not only when the capacity of the condensers C301, C302 are changed, but also when the set data of the D/A converter 322 is changed, or when the comparison reference power sources 329, 330 are changed, it is preferably carried out.

Figure 35:
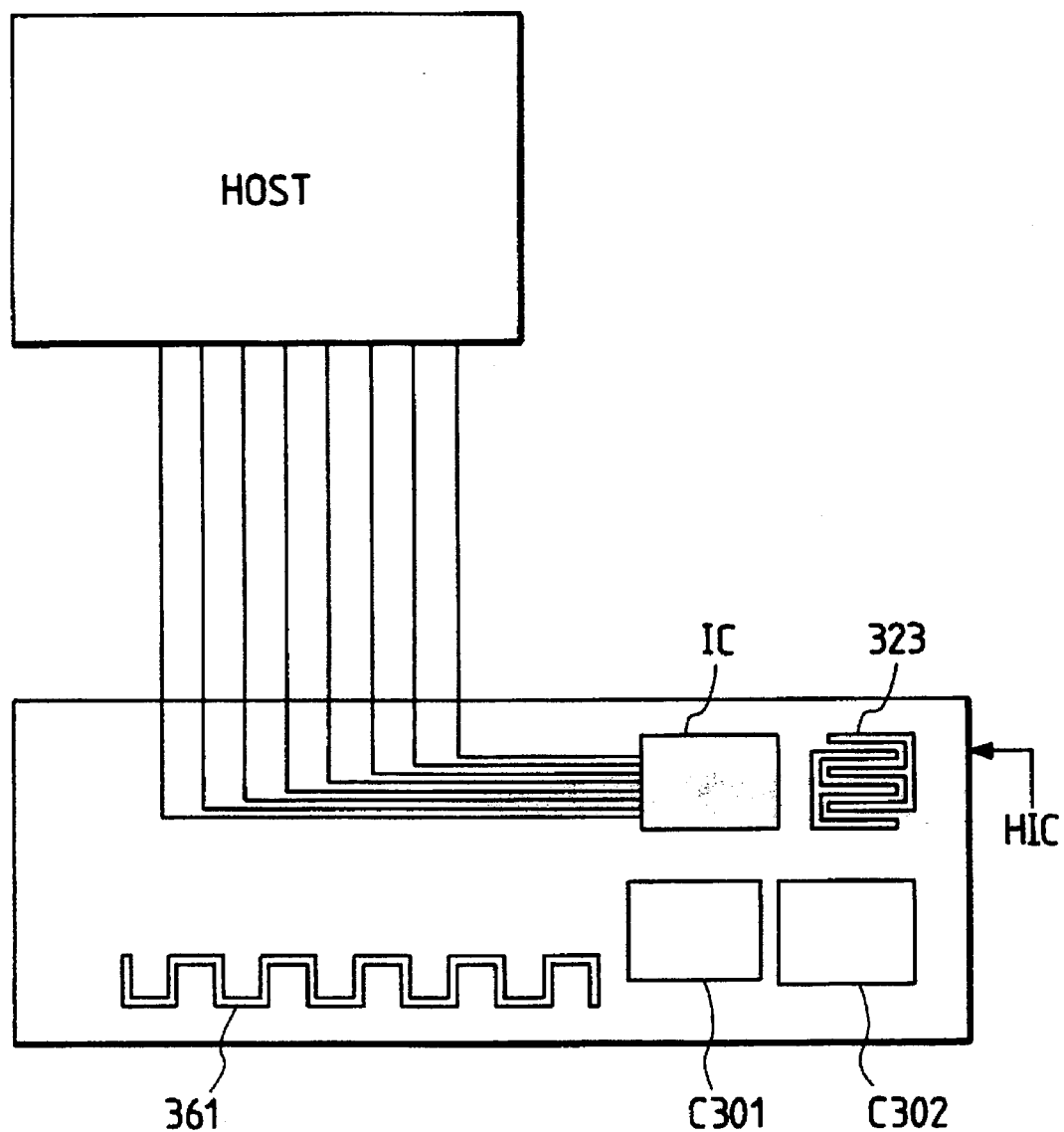
FIG. 35 is a view showing an example of packaging a circuit in the embodiment.

FIG. 35 shows a packaging embodiment. In order to improve the reliability of circuit operation, the operation unit 318 may be an external CPU, and all components are constituted as one-chip IC except for the condensers 311, 312, the precision resistor (reference resistor) 361 and the humidity sensor 323. Specifically, the condensers 311, 312, the precision resistor 361 and the humidity sensor 323 are constituted on the same ceramic substrate to have HIC. And the control lines 342, 343 are led out to its outside to perform the signal processing in the CPU of the host.

In this way, a humidity measuring circuit which is readily fabricated by ICs at a low cost can be realized. Also, the low humidity could not be obtained at high precision by this conventional method, but the humidity measurement is reading allowed at high precision by this method. Also, reverse voltage application means eliminates the possibility that the DC component may be applied from the AC signal applied to the humidity sensor, thereby improving the reliability of the humidity sensor.

EMBODIMENT 13

Figure 37:
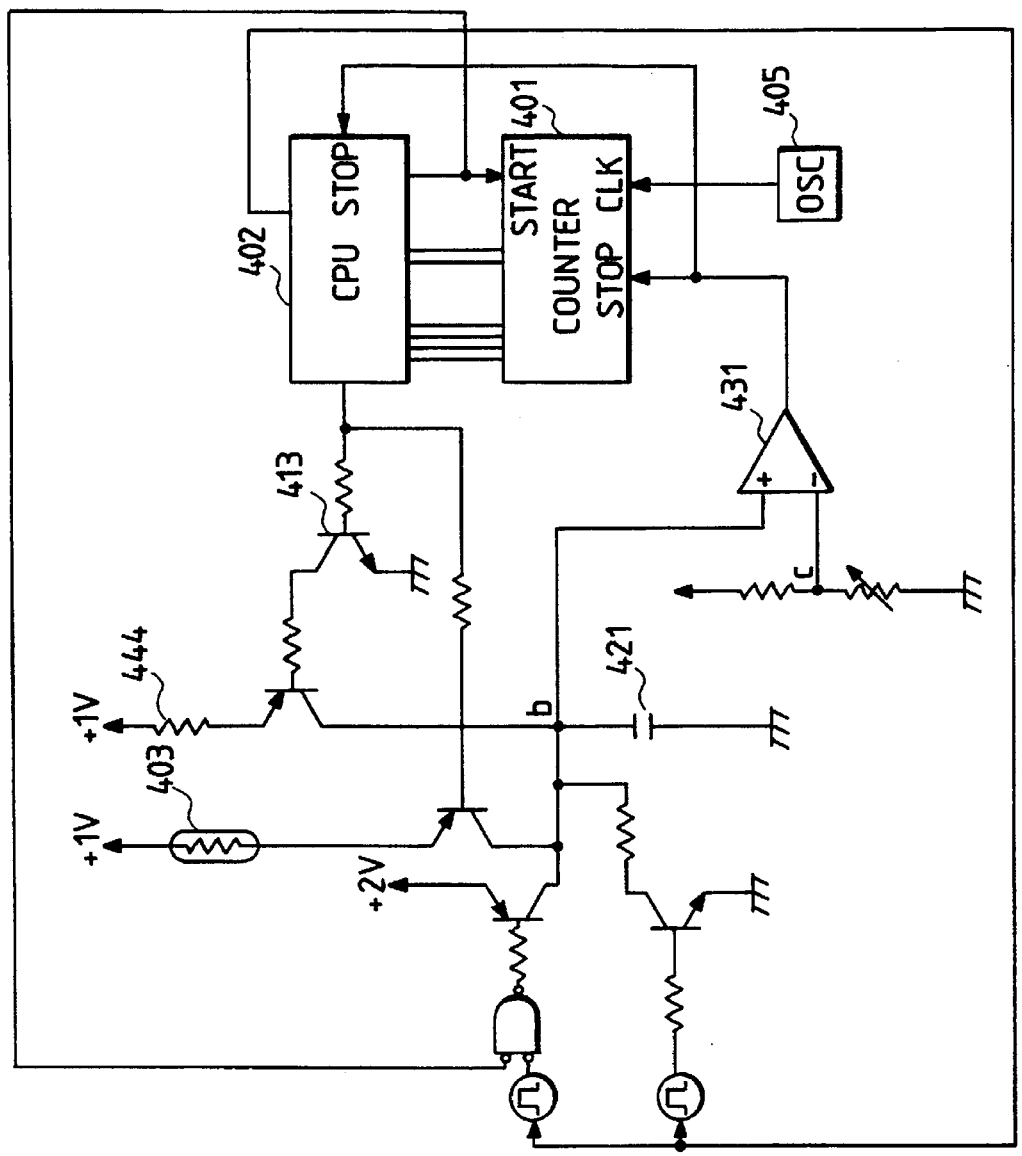
FIG. 37 is a block configuration diagram of a measuring apparatus according to another embodiment of the present invention.
Figure 38:
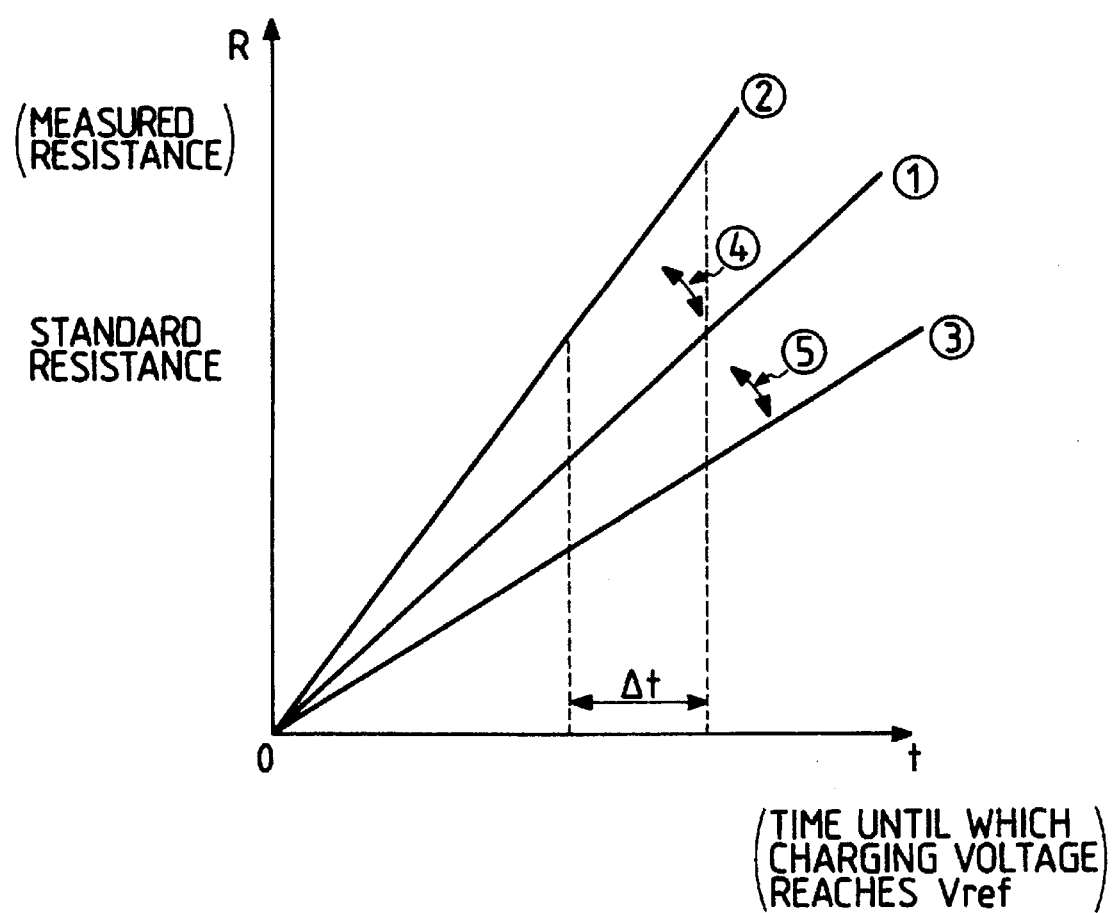
FIG. 38 is a graph showing measurement data.

FIG. 37 is a circuit configuration diagram of a humidity measuring apparatus according to a thirteenth embodiment of the present invention. Element 401 is a counter, element 402 is a central processing unit (CPU), element 403 is a humidity sensor, element 405 is an oscillator for inputting a clock signal to the counter 401, and a standard resistor 444 is 100 MΩ. FIG. 38 shows the measurement data.

① is a resistance of humidity sensor when a condenser 421 indicates a rated value, ② and ③ are resistances of humidity sensor when the rated value of the condenser 421 has changed, and ④ and ⑤ indicate the error.

Figure 39:
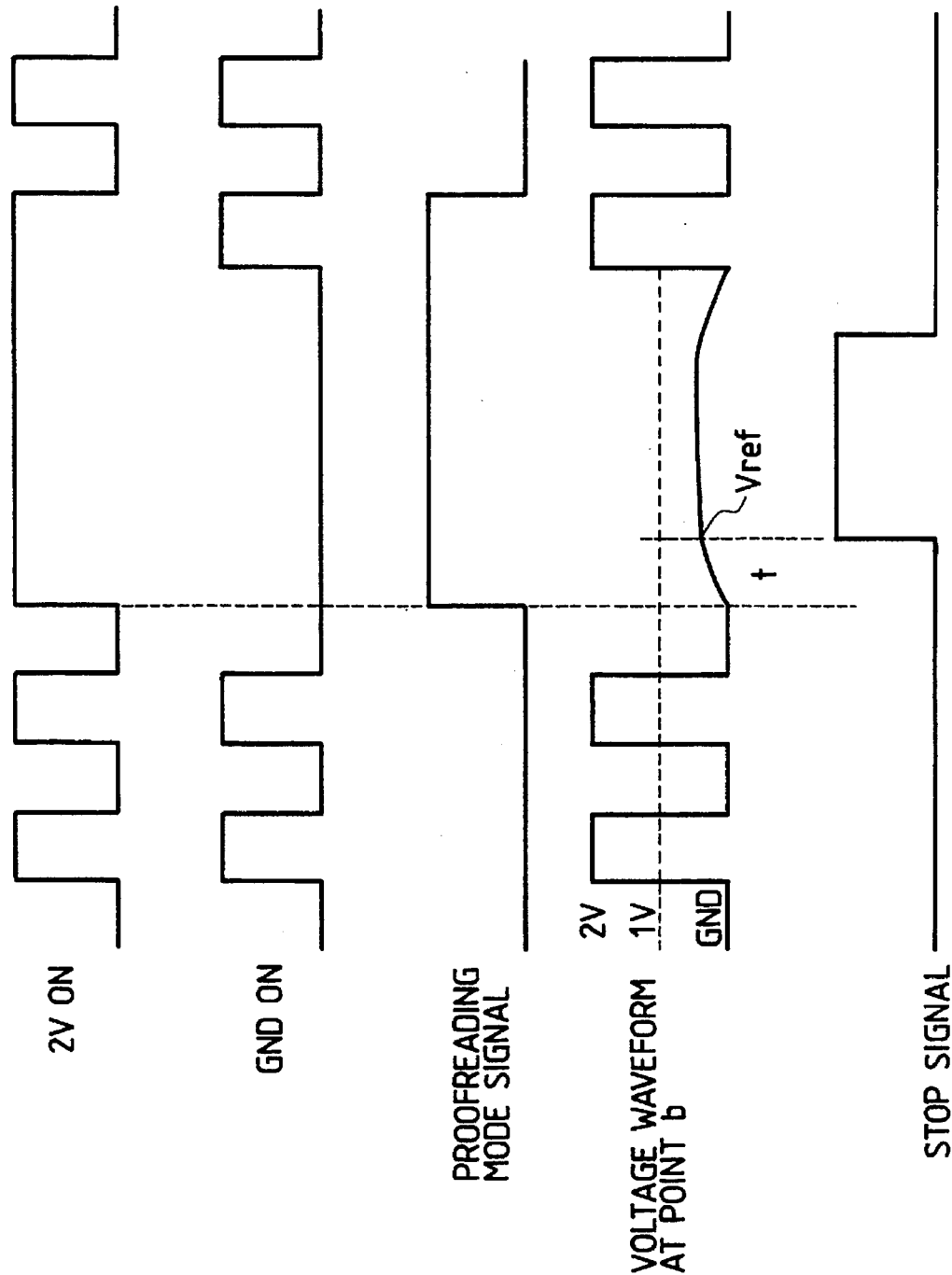
FIG. 39 is a timing chart in the measuring apparatus of FIG. 37.

FIG. 39 is a timing chart in making the measurement. As shown in the timing chart, the AC voltage is applied to be point in FIG. 37. A proofreading mode signal "H" is output from the CPU 402 to a transistor 413. At the same time a counter start signal is output to the counter 401. Thereby, the transistor 413 is turned "OFF", and charging of the condenser is started, and upon reaching the same potential as Vref shown in FIG. 39, "H" signal is output by the comparator 431 (a resistor divided voltage equal to Vref is applied to c point.) to be input to the counter 401 and a stop terminal of the CPU 402.

And the measured value is transmitted to the CPU 402 to measure the time (t) for the charging voltage of condenser 421 to reach Vref within the CPU 402.

Herein, the resistance value of a standard resistor can be obtained by using a linear function r(t)=α·t (r is a measurement resistance value, α is a constant) with the time t as shown in FIG. 39 as a variable.

However, this measurement data will produce an error as indicated ④, ⑤ in FIG. 38 due to the change in the rated value of the condenser 421. Comparing this measurement data with the theoretical data of ① and assuming that the error of t is Δt, and the inclination of ②, ③ is α', α'=γ/(t−Δt) holds (γ is a constant). Next, if a proofreading mode signal from the CPU is made "L", the transistor 413 is turned "ON", and the AC voltage is applied to the humidity sensor 403 and the condenser 421.

Thereafter, the same measurement as above described is performed to obtain the time until charging of the condenser 421 is completed. Based on t and α' thus obtained, the resistance of the humidity sensor 403 can be represented as a linear function, and assuming that the resistance is R, R=α'·t holds. The actual humidity can be obtained by using a function F(R(t)) with R(t) as a variable. The calculation is performed within the CPU 402 to measure the actual humidity. Hence, the highly accurate humidity value can be measured at a low cost by correcting the data measured from the standard resistor to the resistance of the humidity sensor even with the change in the rated value of the condenser 421.

EMBODIMENT 14

Figure 40:
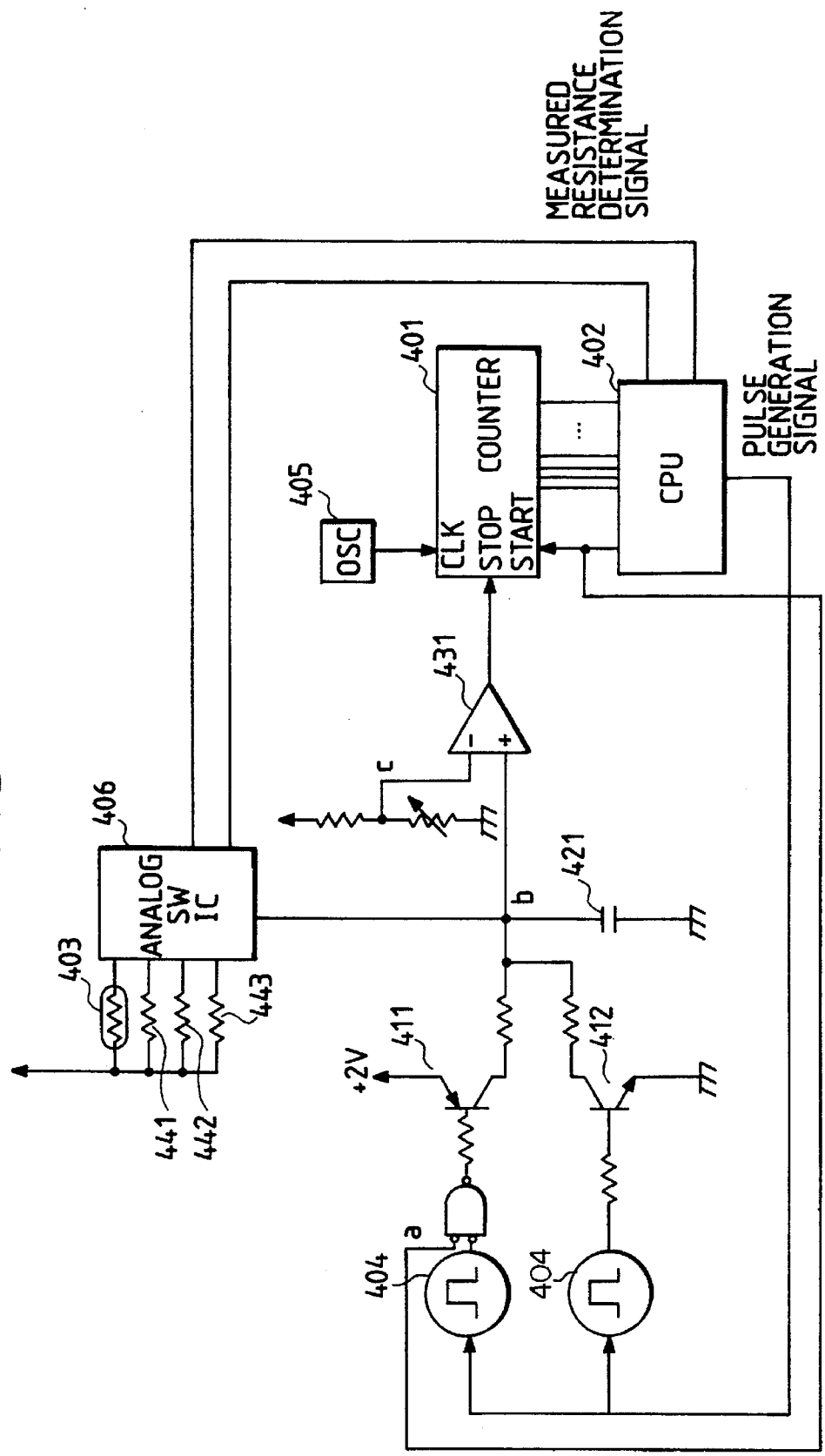
FIG. 40 is a block configuration diagram of a measuring apparatus according to another embodiment of the present invention.

FIG. 40 is a circuit configuration diagram of a humidity measurement apparatus according to a fourteenth embodiment of the present invention. Element 401 is a counter, element 402 is a central processing unit (CPU), 403 is a humidity sensor, elements 404 are pulse generating apparatuses, element 405 is an oscillator for inputting a clock signal to the counter 1, and element 406 is an analog switch IC.

The standard resistors 441, 442, 443 are 10 MΩ, 100 MΩ and 10 GΩ, respectively.

Two-bit signal from the CPU 402 is transmitted to the analog 'switch IC 406 to determine the resistor for the measurement (i.e., a humidity sensor for "00", a resistor 441 for "01" and resistors 442, 443 for "10", "11" respectively).

If an instruction for the pulse generation is input from the CPU 402 to the pulse generating apparatuses 404, the AC voltage is applied to b point via transistors 411, 412. At the same time, it is also applied to a standard resistor 441 and a condenser 421.

A signal for stopping the pulse generation is output from the CPU 402, and a start signal is output to the counter. Then, the condenser 421 starts the charging, and upon reaching the same potential as Vref, H signal is output from a comparator 431 (a resistor divided voltage equal to Vref is input to c point) to stop the counter operation. And the measured value is transmitted to the CPU 402, and the time (t) for the discharge voltage of the condenser 421 to reach a Vref is measured within the CPU 402. This measurement is repeated three times.

Herein, the resistance of the humidity sensor and the actual humidity value can be obtained by using a linear function R1(t)=γ·t+δ (R1 is a standard resistance γ, and δ is a constant) with the time t as a variable as shown in FIG. 38.

With this data, an error from the theoretical data can be obtained in the same way as in the previous embodiment.

Thereafter, the same measurement for the humidity sensor 403 is made to obtain the charging time t of the condenser 421, so that the resistance R of the humidity sensor 403 can be obtained by using R=α'·t+β (α' and β are constants). And the actual humidity can be obtained by using a function F(R(t)) with R(t) as a variable. These calculations are performed within the CPU 402 to measure the actual humidity. Hence, a more accurate humidity can be measured by correcting the data measured from three standard resistors to the resistance of the humidity sensor with the change in the rated value of the condenser 421.

For example, exemplifying a copying machine using the electrophotographic method, a humidity measuring circuit as previously described is provided inside, a switch for enabling the service mode of the copying machine itself is provided on the operation panel of the copying machine for the maintenance, and a humidity sensor proofread mode switch is attached thereto. The serviceman displays the proofread value to the humidity sensor at that time by starting the humidity sensor proofread mode in performing the maintenance, in which if the proofread value is greater than a certain reference value, it is recognized that the degradation of each element has progressed, and the serviceman performs an exchange operation. With these works, the image quality can be highly stabilized.

In this way, a more accurate measurement value can be detected at a low cost by correcting the proofread value obtained by measuring the standard resistor to the measured value of the humidity sensor.

Thereby, for example, an image forming apparatus using the electrophotographic method or a so-called copying machine can treat a high image quality recently developed at a low cost.

The present invention is not limited to a humidity sensor, but is applicable to a thermistor having its resistance varied with the temperature, or a photoconductive cell having its resistance varied with the light quantity by substitution of the thermistor or photoconductive cell for the humidity sensor. It is also applicable to an element having its capacitance or inductance varied depending on the surrounding environment, for example, a microphone having the inductance varied with the sound volume. Or it may be constituted to display the measured value by providing a display unit, or to control an equipment, based on the value measured by connecting to the equipment.

What is claimed is:

1. A measuring apparatus comprising:
   a first element having its impedance nonlinearly varied depending on a state of a surrounding of the first element;
   a second element having a variable impedance which is connected to said first element;
   a voltage source for supplying a potential difference across said first element and said second element, said voltage source including means for reversing a polarity of the potential difference in accordance with an elapse of time;
   a converter for converting a voltage within a predetermined range at a connection point between said first element and said second element into a digital value;
   setting means for setting one of a plurality of impedances in said second element; and
   determining means for determining the surrounding state by performing a line approximation corresponding to the impedances set by said setting means responsive to the digital value for the voltage converted by said converter.

2. The measuring apparatus according to claim 1, wherein said surrounding state is humidity.

3. The measuring apparatus according to claim 1, wherein said surrounding state is temperature.

4. The measuring apparatus according to claim 1, wherein said surrounding state is light quantity.

5. The measuring apparatus according to claim 1, wherein said first element has a variable resistance.

6. The measuring apparatus according to claim 1, wherein said setting means sets an impedance of said second element so that the voltage at the connection point between said first element and said second element falls within a predetermined range.

7. The measuring apparatus according to claim 1, wherein said second element is composed of a plurality of elements having different impedances, and wherein said setting means sets an impedance of said second element by selecting it among said plurality of elements.

8. The measuring apparatus according to claim 1, wherein said voltage source comprises means for applying a DC voltage across said first and second elements when said determining means makes a determination of the surrounding state, and means for applying an AC voltage across said first and second elements except when said determining means makes the determination of the surrounding state.

9. A measuring method comprising the steps of:

supplying a potential difference from a voltage source across a first element having its impedance nonlinearly varied depending on a state of a surrounding of the first element and a second element having a variable impedance connected to the first element, a polarity of the potential difference supplied from the voltage source being reversed in accordance with an elapse of time;

converting a voltage within a predetermined range at a connection point between said first and second elements into a digital value;

setting one of a plurality of impedances in said second element; and determining the surrounding state by performing a line approximation corresponding to the set impedances of said second element based on the digital value of the converted voltage.

10. The measuring method according to claim 9, wherein said surrounding state is humidity.

11. The measuring method according to claim 9, wherein said surrounding state is temperature.

12. The measuring method according to claim 9, wherein said surrounding state is light quantity.

13. The measuring method according to claim 9, wherein said first element has a variable resistance.

14. The measuring method according to claim 9, wherein said setting step includes setting an impedance of said second element so that the voltage at the connection point between the first element and the second element falls within a predetermined range.

15. The measuring method according to claim 9, wherein said second element is composed of a plurality of elements having different impedances, and wherein the setting step includes setting an impedance of said second element by selecting it among the plurality of elements.

16. The measuring method according to claim 9, wherein the supplying of a potential difference from the voltage source includes supplying a DC voltage when a determination is made and supplying an AC voltage when a determination is not made.

17. A measuring apparatus comprising:

a first element having its impedance nonlinearly varied depending on a state of a surrounding of the first element;

a second element having a variable impedance which is connected to the first impedance;

a voltage source for supplying a potential difference across said first element and said second element, said voltage source including means for reversing a polarity of the potential difference in accordance with an elapse of time;

setting means for setting one of a plurality of impedances in said second element; and determining means for determining the surrounding state by performing a line approximation corresponding to the impedances set by said setting means in accordance with a voltage at a connection point between said first element and said second element.

18. A measuring method comprising the steps of:

supplying a potential difference from a voltage source across a first element having its impedance nonlinearly varied depending on a state of a surrounding of the first element and a second element having a variable impedance connected to the first element, a polarity of the potential difference from the voltage source being reversed in accordance with an elapse of time;

setting one of a plurality of impedances in said second element; and determining the surrounding state by performing a line approximation corresponding to the impedances set in said setting step in accordance with a voltage at a connection point between the first element and the second element.

* * * * *

UNITED STATES PATENT AND TRADEMARK OFFICE
CERTIFICATE OF CORRECTION

PATENT NO. : 5,656,928
DATED : Aug. 12, 1997
INVENTOR(S) : SUZUKI ET AL.

It is certified that error appears in the above-identified patent and that said Letters Patent is hereby corrected as shown below:

Column 1

Line 54, "humidity" should read --the humidity--; and
    Line 56, "humidity" should read --the humidity--; and
    Line 57, "condenser" should read --the condenser--.

Column 2

Line 3, "further" should read --a further--; and
    Line 5, "still" should read --a still--; and
    Line 7, "needs" should read --need--; and
    Line 32, "waveform" should read --waveforms--; and
    Line 48, "is a" should read --are--.

Column 5

Line 58, "is" should read --and is--.

Column 6

Line 30, "period," should read --periods,--.

Column 7

Line 45, "preciser" should read --more precise--.

Column 8

Line 19, "make" should read --makes--.

UNITED STATES PATENT AND TRADEMARK OFFICE
CERTIFICATE OF CORRECTION

| | | |
|---|---|---|
| PATENT NO. : | 5,656,928 | Page 2 of 4 |
| DATED : | Aug. 12, 1997 | |
| INVENTOR(S) : | SUZUKI ET AL. | |

It is certified that error appears in the above-identified patent and that said Letters Patent is hereby corrected as shown below:

Column 9

Line 28, "106" should read --Element 106--; and
    Line 62, "counted" (second occurrence) should read --is counted--.

Column 10

Line 12, "of" should read --of the--; and
    Line 13, "RC" should read --the RC--.

Column 11

Line 33, "-V3/E))  should read ---V3/E)))--.

Column 12

Line 31, "is" should read --are--.

Column 13

Line 6, "(1-V153/E)))" should read --1/(1-V153/E)))--; and
    Line 35, "a" (second occurrence) should read --an--.

Column 14

Line 55, "of" should read --of the--; and
    Line 57, "Within" should read --within--.

UNITED STATES PATENT AND TRADEMARK OFFICE
CERTIFICATE OF CORRECTION

PATENT NO. : 5,656,928　　　　　　　　　　Page 3 of 4
DATED : Aug. 12, 1997
INVENTOR(S) : SUZUKI ET AL.

It is certified that error appears in the above-identified patent and that said Letters Patent is hereby corrected as shown below:

Column 16

Line 8, "ends" (both occurrences) should read --end--; and
Line 22, "terminals" should read --terminal--; and
Line 27, "terminals" should read --terminal--; and
Line 52, "terminals" should read --terminal--.

Column 17

Line 63, "of" should be deleted.

Column 18

Line 53, "analog" should read --an analog--.

Column 19

Line 37, "of" should read --of the--; and
Line 38, "of" should read --of the--; and
Line 43, "off" should read --turning off--; and
Line 45, "starts the" should read --starts to--.

Column 20

Line 26, "measurement is" should read --measurement--; and
Line 27, "reading allowed at high precision" should read --reading at high precision is allowed--; and
Line 65, "indicated" should read --indicated by--.

UNITED STATES PATENT AND TRADEMARK OFFICE
CERTIFICATE OF CORRECTION

PATENT NO. : 5,656,928
DATED : Aug. 12, 1997
INVENTOR(S) : SUZUKI ET AL.

It is certified that error appears in the above-identified patent and that said Letters Patent is hereby corrected as shown below:

<u>Column 21</u>

```
Line 23, "403" should read --element 403--; and
Line 31, "Two-bit" should read --A two-bit--; and
Line 32, "'switch" should read --switch--.
```

Signed and Sealed this

Ninth Day of June, 1998

Attest:

BRUCE LEHMAN

*Attesting Officer*     *Commissioner of Patents and Trademarks*